United States Patent
Stark et al.

(10) Patent No.: US 10,327,846 B1
(45) Date of Patent: Jun. 25, 2019

(54) METHODS FOR TREATING VASCULAR STENOSES INCLUDING LASER ATHERECTOMY AND DRUG DELIVERY VIA DRUG-COATED BALLOONS

(71) Applicant: The Spectranetics Corporation, Colorado Springs, CO (US)

(72) Inventors: Matthew Stark, Castle Rock, CO (US); Diane Gorder, Monument, CO (US); Timothy J. Hale, Castle Rock, CO (US); Blaine Schneider, Colorado Springs, CO (US)

(73) Assignee: THE SPECTRANETICS CORPORATION, Colorado Springs, CO (US)

( * ) Notice: Subject to any disclaimer, the term of this patent is extended or adjusted under 35 U.S.C. 154(b) by 129 days.

(21) Appl. No.: 15/246,815

(22) Filed: Aug. 25, 2016

Related U.S. Application Data

(60) Provisional application No. 62/209,691, filed on Aug. 25, 2015.

(51) Int. Cl.
*A61B 18/20* (2006.01)
*A61B 18/24* (2006.01)
(Continued)

(52) U.S. Cl.
CPC ............ *A61B 18/245* (2013.01); *A61L 29/08* (2013.01); *A61L 29/16* (2013.01); *A61M 25/104* (2013.01);
(Continued)

(58) Field of Classification Search
CPC ........ A61B 18/245; A61B 2018/00172; A61B 2018/00267; A61B 2018/00345;
(Continued)

(56) References Cited

U.S. PATENT DOCUMENTS 8,396,548 B2    3/2013  Perry
2003/0009157 A1  1/2003  Levine
(Continued)

FOREIGN PATENT DOCUMENTS

EP    0820786 A2    1/1998
WO   2006006169 A2  1/2006
(Continued)

*Primary Examiner* — Aaron F Roane

(57) ABSTRACT

A method for treating a stenosis includes providing a laser ablation system including a laser catheter, the laser catheter including a distal end having a plurality of laser emitters; positioning the distal end of the laser catheter within the subject proximate the target vascular portion; delivering laser energy to the laser catheter and emitting the laser energy from the plurality of laser emitters to ablate the stenosis; withdrawing the laser catheter from the subject; providing a balloon system including a drug-coated balloon, the balloon carrying at least one therapeutic agent, the therapeutic agent being a restenosis inhibitor; positioning the balloon within the subject proximate the target vascular portion; expanding the balloon to engage the target vascular portion; delivering the therapeutic agent from the balloon to the target vascular portion; delivering the therapeutic agent from the balloon to the target vascular portion; and withdrawing the balloon from the subject.

14 Claims, 8 Drawing Sheets

(51) Int. Cl.
*A61M 25/10* (2013.01)
*A61L 29/08* (2006.01)
*A61L 29/16* (2006.01)
*A61B 18/22* (2006.01)
*A61B 18/00* (2006.01)

(52) U.S. Cl.
CPC ............... *A61B 2018/00172* (2013.01); *A61B 2018/00267* (2013.01); *A61B 2018/00345* (2013.01); *A61B 2018/00577* (2013.01); *A61B 2018/2261* (2013.01); *A61B 2018/2266* (2013.01); *A61L 2300/416* (2013.01); *A61L 2300/606* (2013.01); *A61M 2025/105* (2013.01)

(58) Field of Classification Search
CPC .. A61B 2018/00577; A61B 2018/2261; A61B 2018/2266; A61L 29/08; A61L 29/16; A61L 2300/416; A61L 2300/606; A61M 25/104; A61M 2025/105
USPC .......................................................... 606/2
See application file for complete search history.

(56) References Cited

U.S. PATENT DOCUMENTS

| | | |
|---|---|---|
| 2012/0221013 A1 | 8/2012 | Hawkins |
| 2012/0303011 A1 | 11/2012 | Schaeffer |
| 2013/0030447 A1 | 1/2013 | Adams |
| 2013/0197555 A1 | 8/2013 | Schaer |
| 2013/0282084 A1* | 10/2013 | Mathur ............... A61N 5/00 607/101 |
| 2014/0039513 A1 | 2/2014 | Hakala |
| 2014/0133814 A1 | 5/2014 | Stevens |
| 2014/0214061 A1 | 7/2014 | Adams |
| 2015/0105714 A1* | 4/2015 | Laudenslager ...... A61B 18/245 604/20 |

FOREIGN PATENT DOCUMENTS

| | | |
|---|---|---|
| WO | 2011006017 A1 | 1/2011 |
| WO | 2013169807 A1 | 11/2013 |
| WO | 2014163955 A1 | 10/2014 |

* cited by examiner

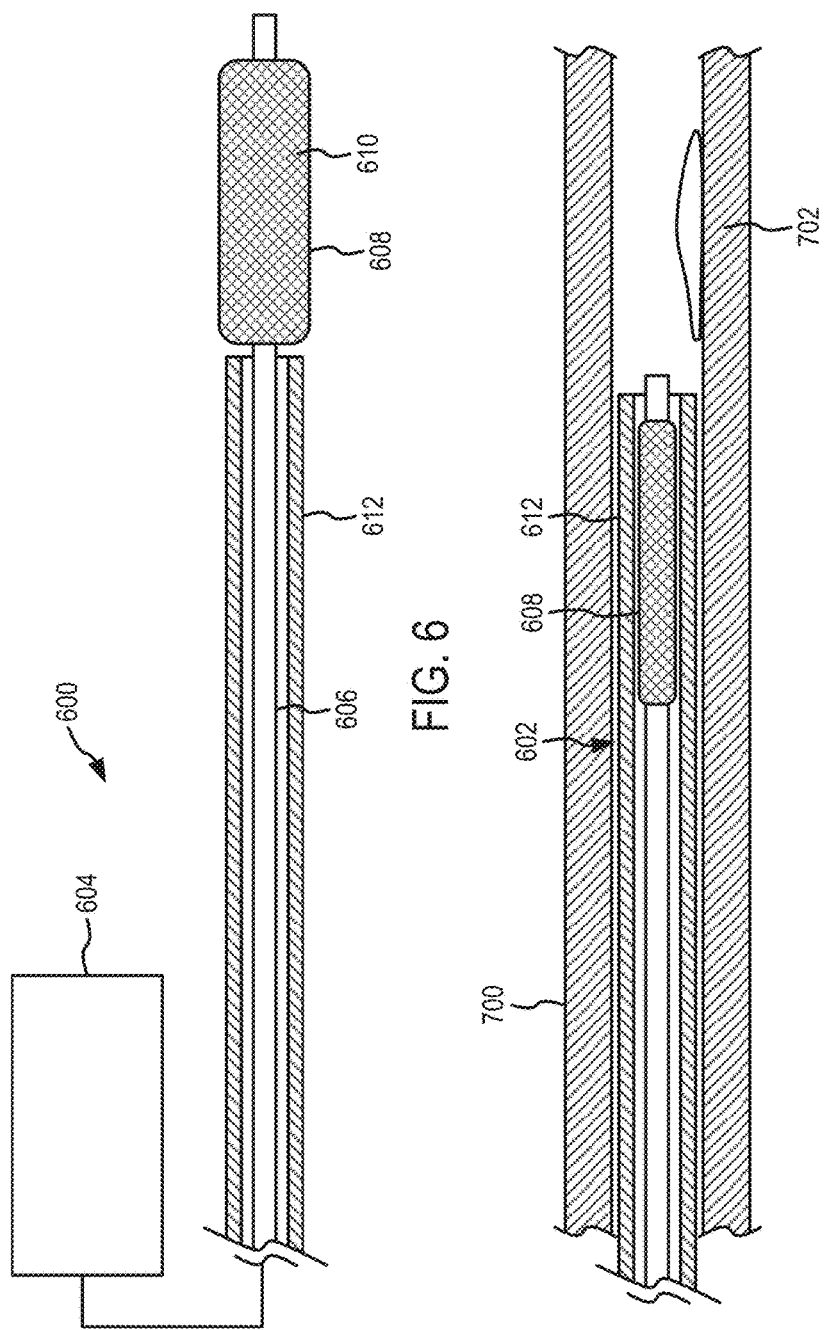

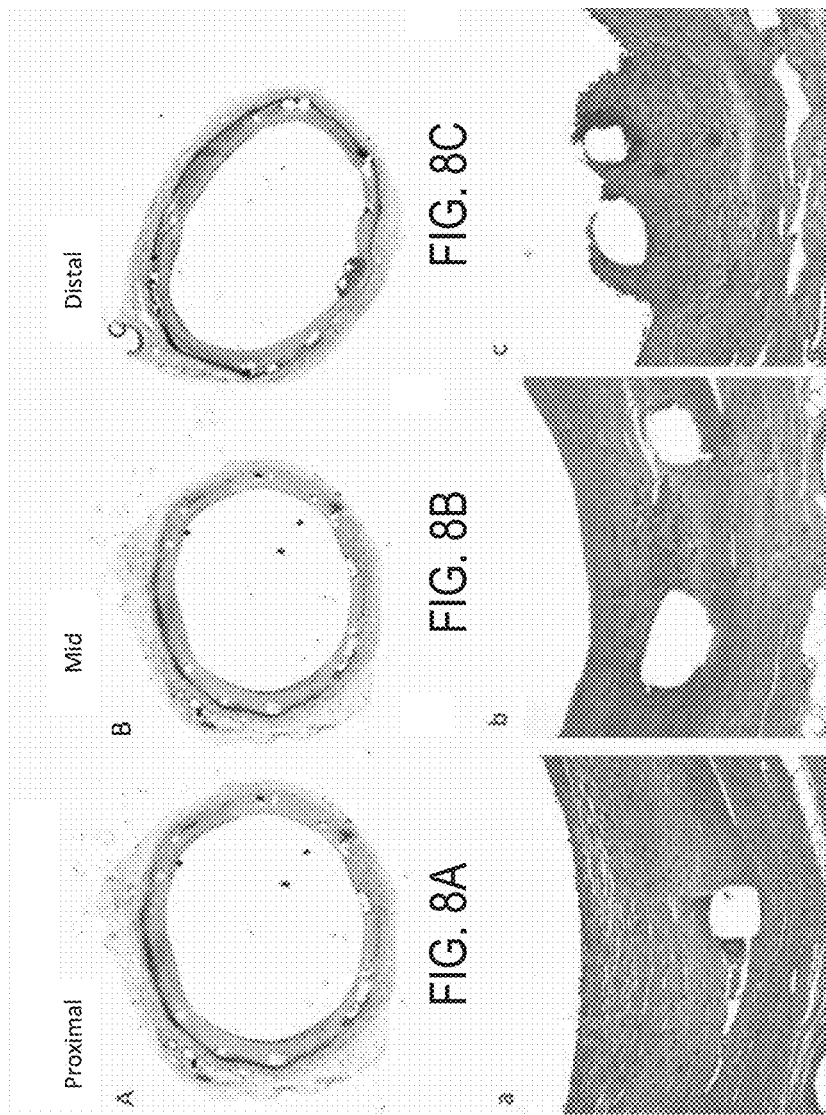

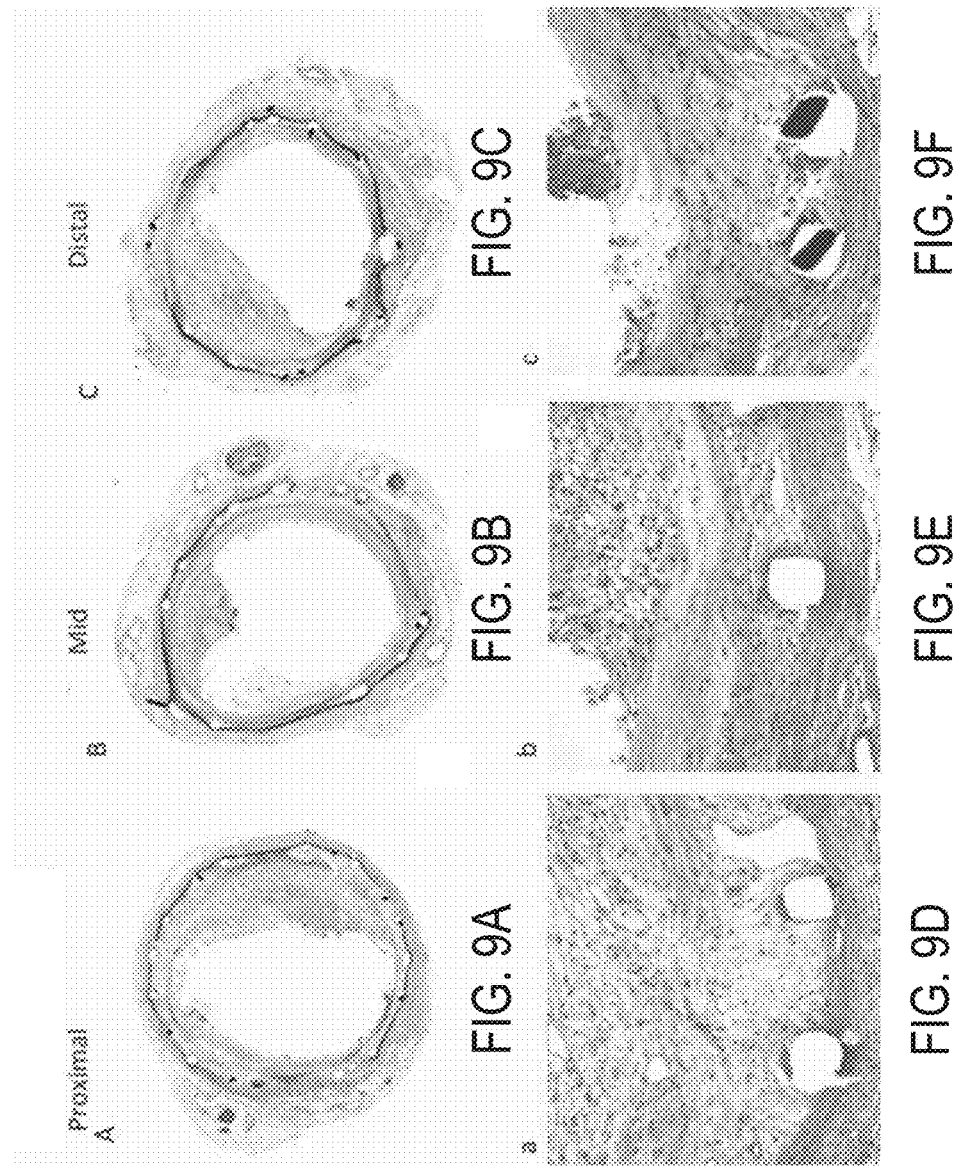

METHODS FOR TREATING VASCULAR STENOSES INCLUDING LASER ATHERECTOMY AND DRUG DELIVERY VIA DRUG-COATED BALLOONS

CROSS REFERENCE TO RELATED APPLICATION

The present application claims the benefit of and priority to, under 35 U.S.C. § 119(e), U.S. Provisional Application Ser. No. 62/209,691, filed Aug. 25, 2015, entitled METHODS FOR TREATING VASCULAR STENOSES INCLUDING LASER ATHERECTOMY AND DRUG DELIVERY VIA DRUG-COATED BALLOONS, which is hereby incorporated herein by reference in its entirety for all that it teaches and for all purposes.

FIELD OF THE DISCLOSURE

The present disclosure relates generally to the use of medical devices for the treatment of vascular conditions. In particular, the present disclosure provides methods for treating vascular stenoses by using laser atherectomy and delivering therapeutic agents via balloon catheters to the stenoses.

BACKGROUND

Peripheral artery disease (PAD) affects millions of Americans. PAD most often results from a condition known as atherosclerosis, which generally manifests as the accumulation of a waxy substance on the inside of a subject's arteries. This substance, called plaque, is made of cholesterol, fatty compounds, calcium, and a blood-clotting material called fibrin. As the plaque builds up, the artery narrows, or becomes stenotic, making it more difficult for blood to flow through the peripheral arteries. The reduced blood flow limits the amount of oxygen that is delivered to the extremities, which in turn may cause pain in the extremities and, in severe cases, gangrene, which may ultimately require amputation.

Balloon angioplasty and other transluminal medical treatments are well-known and have been proven efficacious in the treatment of stenotic lesions at the core of PAD. In a typical angioplasty procedure, a catheter is inserted into the groin or arm of a subject and guided to the affected arteries. There, blocked (partially blocked or fully blocked) arteries can be unblocked by increasing the size of the passageway within the artery with a balloon positioned at the tip of the catheter. Initially, angioplasty was performed only with balloon catheters, but technical advances have been made and improved patient outcomes have been achieved with the placement of small metallic spring-like devices called "stents" at the site of the blockage. The implanted stent serves as a scaffold that keeps the artery open. Angioplasty and stenting techniques are widely used around the world and provide an alternative option to bypass surgery for improving peripheral blood flow. There are, however, limitations associated with angioplasty and stenting, one of which is called "restenosis."

Restenosis occurs when the treated vessel becomes blocked again—when the stenosis reforms within the vessel. For example, when a stent is placed in a blood vessel, new tissue grows inside the stent, covering the struts of the stent. Initially, this new tissue consists of healthy cells from the lining of the arterial wall (that is, endothelium). This is a favorable effect because development of normal lining over the stent allows blood to flow smoothly over the stented area without clotting. Later, scar tissue may form underneath the new healthy lining. However, in about 25 percent of patients, the growth of scar tissue underneath the lining of the artery may be so thick that it can obstruct the blood flow and produce another blockage. "In-stent" restenosis is typically seen 3 to 6 months after the initial procedure.

In addition to angioplasty and the deployment of stents, other types of intervention for stenotic vessels include atherectomy, bypass surgery, and the use of laser ablation and mechanical cutting systems to reduce the plaque size. Treatments using various pharmacological agents have also been developed, including medical infusions, drug-eluding stents (DES), and drug-coated balloons (DCB).

SUMMARY

Given the persistence of PAD, however, the most efficacious means for improving therapeutic outcomes may involve combinations of therapies designed not only to reduce plaque size in the short term, but also to prevent future complications such as restenosis. Combinatorial therapies may offer the best chance to improve therapeutic outcomes for people suffering from PAD. These and other needs are addressed by the various aspects, embodiments, and configurations of the present disclosure.

Methods according to the present disclosure generally relate to treating vascular stenoses (for example, scar tissue, plaque build-up, calcium deposits and other types of undesirable lesion) by using laser atherectomy and drug delivery via drug-coated balloons. It is believed that such methods may be more effective for treating stenoses and preventing restenosis than methods that include balloon angioplasty and drug delivery via drug-coated balloons.

In some embodiments, the present disclosure is directed to a method for treating a target vascular portion of a subject including a stenosis formed by the presence of a thrombus within the vasculature. The method includes providing a laser ablation system including a laser catheter, the laser catheter including a distal end having a plurality of laser emitters; positioning the distal end of the laser catheter within the subject proximate the target vascular portion; delivering laser energy to the laser catheter and emitting the laser energy from the plurality of laser emitters to ablate the stenosis; withdrawing the laser catheter from the subject; providing a balloon system including a drug-coated balloon, the drug-coated balloon carrying at least one therapeutic agent, the at least one therapeutic agent being a restenosis inhibitor; positioning the drug-coated balloon within the subject proximate the target vascular portion; expanding the drug-coated balloon to engage the target vascular portion; delivering the at least one therapeutic agent from the drug-coated balloon to the target vascular portion; delivering the at least one therapeutic agent from the drug-coated balloon to the target vascular portion; and withdrawing the drug-coated balloon from the subject.

A method as described herein above, wherein the restenosis inhibitor includes paclitaxel.

A method as described herein above, wherein the laser ablation system includes a laser generator, and further comprising delivering the laser energy from the laser generator to the laser catheter.

A method described herein above, wherein the target vascular portion of the subject includes a stent coupled to the stenosis, and wherein emitting the laser energy from the plurality of laser emitters to ablate the stenosis includes emitting the laser energy from the plurality of laser emitters to ablate the stenosis within the stent.

A method described herein above, wherein emitting the laser energy from the plurality of laser emitters to ablate the stenosis includes: emitting the laser energy at a first intensity; and emitting the laser energy at a second intensity, the second intensity being different than the first intensity.

A method described herein above, wherein the second intensity is greater than the first intensity.

A method described herein above, wherein emitting the laser energy from the plurality of laser emitters to ablate the stenosis includes: emitting the laser energy at a first repetition rate; and emitting the laser energy at a second repetition rate, the second repetition rate being different than the first repetition rate.

A method described herein above, wherein the second repetition rate is greater than the first repetition rate.

A method described herein above, wherein the laser catheter is a first laser catheter having a first external diameter, the plurality of laser emitters is a first plurality of laser emitters, wherein the laser ablation system further includes a second laser catheter including a distal end having a second plurality of laser emitters, the second laser catheter having a second external diameter, the second external diameter being different than the first external diameter, and further comprising: positioning the distal end of the second laser catheter within the subject proximate the target vascular portion; delivering laser energy to the second laser catheter and emitting the laser energy from the second plurality of laser emitters to ablate the stenosis; and withdrawing the second laser catheter from the subject.

A method described herein above, wherein the second external diameter is greater than the first external diameter.

The details of the methods discussed herein generally relate to PAD, but the methods are also applicable for treating coronary artery disease (CAD).

These and other advantages will be apparent from the disclosure of the aspects, embodiments, and configurations contained herein.

As used herein, "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together. When each one of A, B, and C in the above expressions refers to an element, such as X, Y, and Z, or class of elements, such as $X_1$-$X_n$, $Y_1$-$Y_m$, and $Z_1$-$Z_o$, the phrase is intended to refer to a single element selected from X, Y, and Z, a combination of elements selected from the same class (for example, $X_1$ and $X_2$) as well as a combination of elements selected from two or more classes (for example, $Y_1$ and $Z_o$).

It is to be noted that the term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The terms "vasculature" and "vascular" as used herein refer to any part of the circulatory system of a subject, including peripheral and non-peripheral arteries and veins. Vascular material found within the vasculature can be comprised of both biological material (for example, nucleic acids, amino acids, carbohydrates, polysaccharides, lipids and the like) and non-biological material (for example, fat deposits, fibrous tissue, calcium deposits, remnants of dead cells, cellular debris and the like).

A "catheter" is a tube that can be inserted into a body cavity, duct, lumen, or vessel, such as the vasculature system. In most uses, a catheter is a relatively thin, flexible tube ("soft" catheter), though in some uses, it may be a larger, solid-less flexible—but possibly still flexible—catheter ("hard" catheter).

A "laser emitter" refers to an end portion of a fiber or an optical component that emits laser energy from a distal end of the catheter towards a desired target, which is typically a portion of the vasculature that includes a stenosis formed by scar tissue, plaque build-up, calcium deposits and/or other types of undesirable lesion.

An optical fiber (or laser active fibre) is a flexible, transparent fiber made of an optically transmissive material, such as glass (silica) or plastic, which functions as a waveguide, or "light pipe", to transmit energy between the two ends of the fiber.

A "coupler" or "fiber optic coupler" refers to the optical fiber device with one or more input fibers and one or several output fibers. Fiber couplers are commonly special optical fiber devices with one or more input fibers for distributing optical signals into two or more output fibers. Optical energy is passively split into multiple output signals (fibers), each containing light with properties identical to the original except for reduced amplitude. Fiber couplers have input and output configurations defined as M×N. M is the number of input ports (one or more). N is the number of output ports and is always equal to or greater than M. Fibers can be thermally tapered and fused so that their cores come into intimate contact. This can also be done with polarization-maintaining fibers, leading to polarization-maintaining couplers (PM couplers) or splitters. Some couplers use side-polished fibers, providing access to the fiber core. Couplers can also be made from bulk optics, for example in the form of microlenses and beam splitters, which can be coupled to fibers ("fiber pig-tailed").

The term "balloon catheter" as used herein generally refers to the various types of angioplasty catheters which carry a balloon for performing angioplasty. Balloon catheters may also be of a wide variety of inner structure, such as different lumen design, of which there are at least three basic types: triple lumen, dual lumen and co-axial lumen. All varieties of internal structure and design variation are meant to be included by use of the term "balloon catheter" herein.

The term "amphiphilic" as used herein generally refers to a material that at least partially dissolvable in aqueous solvents, such as blood in-vivo, as well as at least partially dissolvable in non-aqueous solvents, such as ethanol, methanol, and/or isopropanol.

The term "stenosis" as used herein generally refers to an abnormal narrowing in a blood vessel, the vasculature or other tubular organ or structure. There are many causes of a stenosis. One cause is atherosclerosis (also known as arteriosclerotic vascular disease), which is a specific form of arteriosclerosis in which a vasculature wall thickens as a result of invasion and accumulation of white blood cells. The thickening of the wall can lead to the formation of a thrombus within the lumen of the vasculature, whereby the thrombus may fully or partially occlude the lumen. "Restenosis" is the recurrence of stenosis after a procedure to initially treat the stenosis.

The term "therapeutic agent" as used herein generally refers to any known or hereafter discovered pharmacologically active agent that provides therapy to a subject through the alleviation of one or more of the subject's physiological symptoms. A therapeutic agent may be a compound that occurs in nature, a chemically modified naturally occurring compound, or a compound that is chemically synthesized. The agent will typically be chosen from the generally recognized classes of pharmacologically active agents, including the following: analgesic agents; anesthetic agents; antiarthritic agents; respiratory drugs, including antiasthmatic agents; anticancer agents, including antineoplastic drugs; anticholinergics; anticonvulsants; antidepressants; antidiabetic agents; antidiarrheals; antihelminthics; antihistamines; antihyperlipidemic agents; antihypertensive agents; anti-infective agents such as antibiotics and antiviral agents; antiinflammatory agents; antimigraine preparations; antinauseants; antiparkinsonism drugs; antipruritics; antipsychotics; antipyretics; antispasmodics; antitubercular agents; antiulcer agents; antiviral agents; anxiolytics; appetite suppressants; attention deficit disorder (ADD) and attention deficit hyperactivity disorder (ADHD) drugs; cardiovascular preparations including calcium channel blockers, CNS agents; beta-blockers and antiarrhythmic agents; central nervous system stimulants; cough and cold preparations, including decongestants; diuretics; genetic materials; herbal remedies; hormonolytics; hypnotics; hypoglycemic agents; immunosuppressive agents; leukotriene inhibitors; mitotic inhibitors; restenosis inhibitors; muscle relaxants; narcotic antagonists; nicotine; nutritional agents, such as vitamins, essential amino acids and fatty acids; ophthalmic drugs such as antiglaucoma agents; parasympatholytics; psychostimulants; sedatives; steroids; sympathomimetics; tranquilizers; and vasodilators including general coronary, peripheral and cerebral.

The term "means" as used herein shall be given its broadest possible interpretation in accordance with 35 U.S.C., Section 112(f). Accordingly, a claim incorporating the term "means" shall cover all structures, materials, or acts set forth herein, and all of the equivalents thereof. Further, the structures, materials or acts and the equivalents thereof shall include all those described in the summary, brief description of the drawings, detailed description, abstract, and claims themselves.

It should be understood that every maximum numerical limitation given throughout the present disclosure is deemed to include each and every lower numerical limitation as an alternative, as if such lower numerical limitations were expressly written herein. Every minimum numerical limitation given throughout the present disclosure is deemed to include each and every higher numerical limitation as an alternative, as if such higher numerical limitations were expressly written herein. Every numerical range given throughout the present disclosure is deemed to include each and every narrower numerical range that falls within such broader numerical range, as if such narrower numerical ranges were all expressly written herein.

The preceding is a simplified summary of the disclosure to provide an understanding of some aspects of the disclosure. This summary is neither an extensive nor exhaustive overview of the disclosure and its various aspects, embodiments, and configurations. It is intended neither to identify key or critical elements of the disclosure nor to delineate the scope of the disclosure but to present selected concepts of the disclosure in a simplified form as an introduction to the more detailed description presented below. As will be appreciated, other aspects, embodiments, and configurations of the disclosure are possible utilizing, alone or in combination, one or more of the features set forth above or described in detail below.

BRIEF DESCRIPTION OF THE DRAWINGS

The accompanying drawings are incorporated into and form a part of the specification to illustrate several examples of the present disclosure. These drawings, together with the description, explain the principles of the disclosure. The drawings simply illustrate preferred and alternative examples of how the disclosure can be made and used and are not to be construed as limiting the disclosure to only the illustrated and described examples. Further features and advantages will become apparent from the following, more detailed, description of the various aspects, embodiments, and configurations of the disclosure, as illustrated by the drawings referenced below.

FIG. 6 is a schematic view of an exemplary embodiment of a balloon system in accordance with the present disclosure; a balloon of a balloon catheter of the system is illustrated in an expanded configuration and a distally advanced position relative to a protective sheath;

FIG. 7A is an elevation longitudinal section view of the balloon catheter of FIG. 6 longitudinally offset from a target to be treated; the balloon is in an unexpanded configuration and a proximally retracted position within the protective sheath;

FIGS. 8A-8F are cross-sectional views of carotid artery segments of a rabbit subjected to treatment by laser ablation and drug-coated balloon systems; and FIGS. 9A-9F are cross-sectional views of carotid artery segments of a rabbit subjected to treatment by balloon angioplasty and drug-coated balloon systems.

DETAILED DESCRIPTION

Methods according to the present disclosure generally relate to treating vascular stenoses (for example, scar tissue, plaque build-up, calcium deposits and other types of undesirable lesion) by using laser atherectomy and drug delivery via drug-coated balloons. It is believed that such methods may be more effective for treating stenoses and preventing restenosis than methods that include balloon angioplasty and drug delivery via drug-coated balloons.

Figure 1:
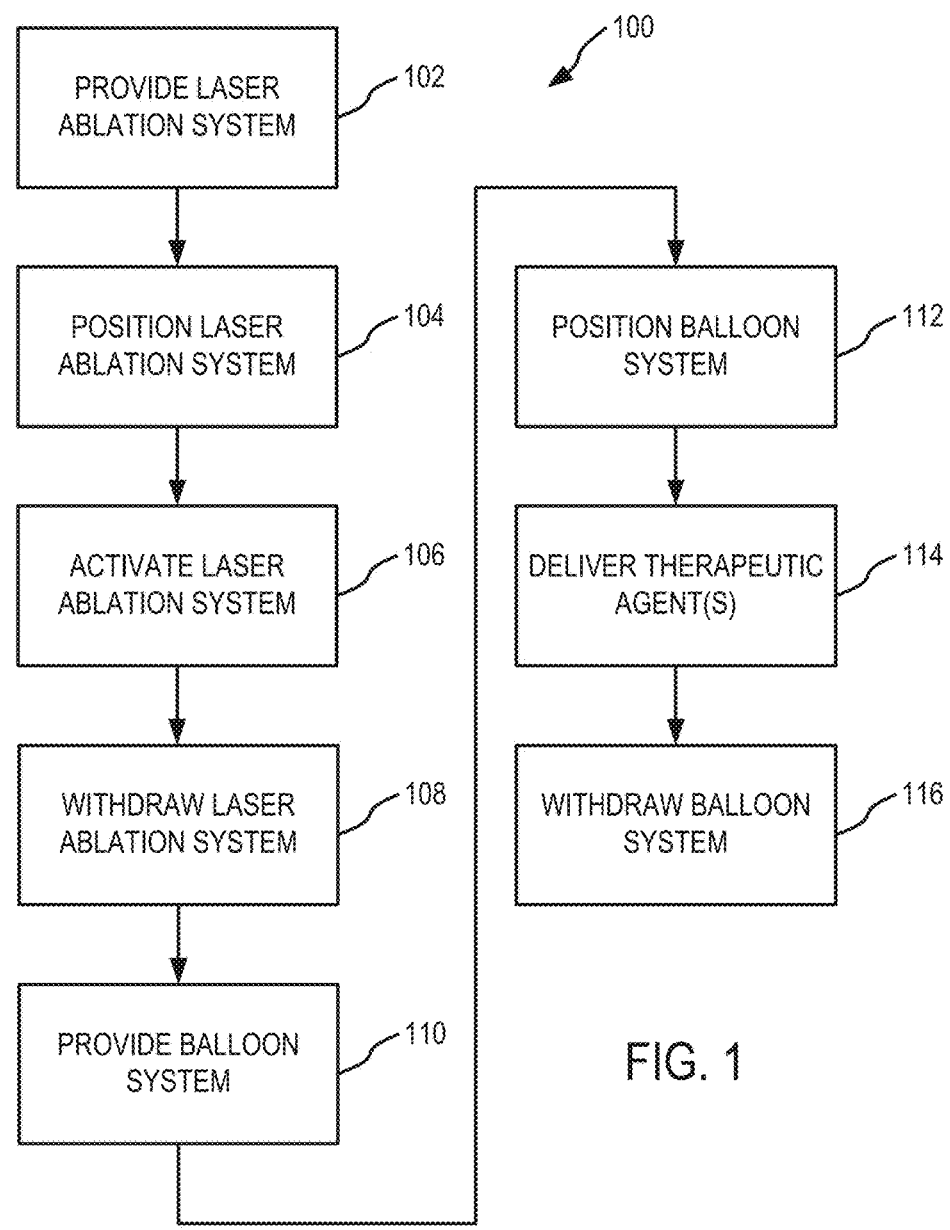
FIG. 1 is a flow diagram of an exemplary method for treating vascular stenoses by using laser atherectomy and drug delivery via drug-coated balloons in accordance with the present disclosure.

FIG. 1 is a flow diagram 100 of an exemplary method for treating vascular stenoses by using laser atherectomy and drug delivery via drug-coated balloons in accordance with the present disclosure. Generally, the method may be performed under fluoroscopy to provide images of the vasculature and positions of medical devices in the vasculature. The method begins at block 102 by providing a laser ablation system. Generally and in some embodiments, the laser ablation system includes a laser catheter that is inserted into and transmits laser energy to a target portion of the vasculature to ablate a stenosis. In some embodiments, the laser ablation system also includes a laser generator that delivers laser energy to the laser catheter.

Examples of laser catheters in accordance with the present disclosure include those available from The Spectranetics Corporation of Colorado Springs, Colo. under the tradenames ELCA™ and Turbo-Elite™. Further examples of laser catheters in accordance with the present disclosure include those disclosed in U.S. Pat. Nos. 5,267,993, 5,383,199, and co-pending application U.S. patent application Ser. No. 13/804,812, the entireties of which are incorporated by reference herein for all purposes. Each of the above laser catheters is typically used for coronary intervention or catheterization such as recanalizing occluded arteries, changing lesion morphology, and facilitating stent placement. The working (distal) end of a laser catheter typically has a plurality of laser emitters that emit laser energy and ablate the targeted vascular portion, namely a thrombus within the lumen of the vasculature. The opposite (proximal) end of a laser catheter typically has a fiber optic coupler, which detachably couples to the laser generator.

Figure 3:
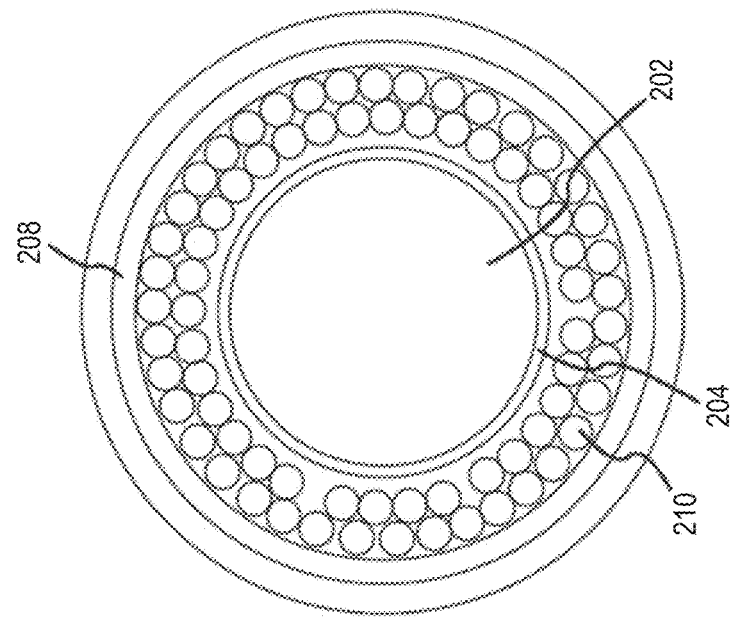
FIG. 3 is an elevation view of the distal end of the laser catheter of FIG. 2.
Figure 2:
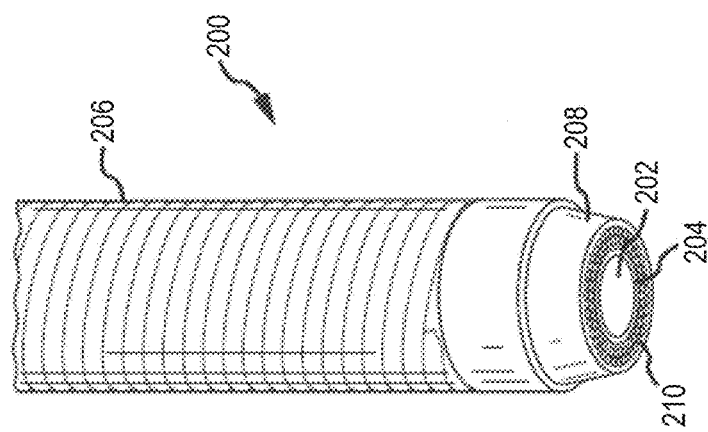
FIG. 2 is a perspective view of a distal end of an exemplary embodiment of a laser catheter in accordance with the present disclosure.
Figure 4:
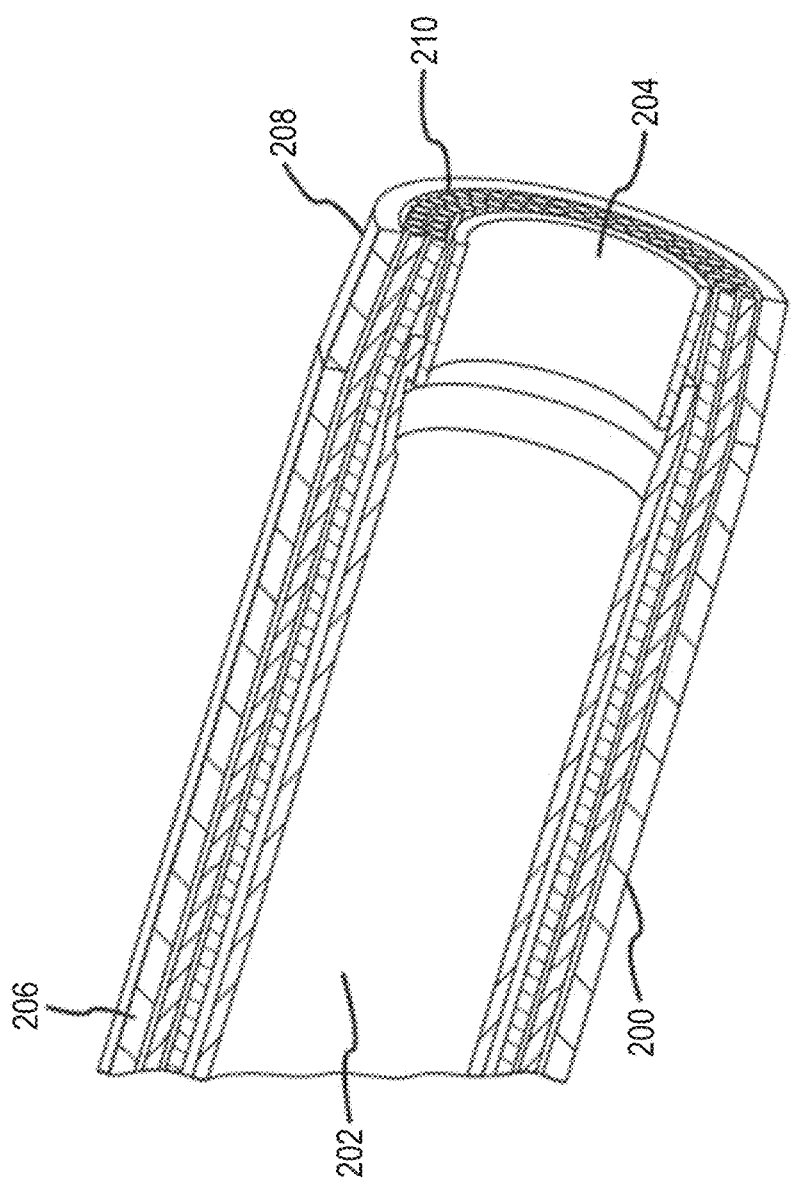
FIG. 4 is a perspective longitudinal section view of the distal end of the laser catheter of FIG. 2.

Referring now to FIGS. 2-4, a distal end of an exemplary embodiment of a laser catheter 200 in accordance with the present disclosure is illustrated. The laser catheter 200 may (as depicted in FIGS. 2-4) or may not include a lumen 202. If a lumen 202 is included in the laser catheter 200, a clinician may slide the laser catheter over a guidewire (not illustrated) through lumen 202. In some embodiments, however, the catheter 200 may have a separate guidewire lumen (not illustrated) located between an inner band 204 and an outer jacket 206. Incorporation of such a guidewire lumen is generally known to one of ordinary skill in the art, and all such guidewire lumens are within the knowledge of one skilled in the art are considered within the scope of the present disclosure.

The proximal end (not illustrated) of the catheter 200 is attached to a coupler (not illustrated) and includes the outer jacket 206, an inner band, and a plurality of laser transmitters (for example, optical fibers 210) similar to the configuration and orientation of the laser emitters depicted in FIGS. 2-4. The distal end of the catheter 200 includes a tapered outer band 208, which is attached to the distal end of the outer jacket 206, a plurality of laser emitters (for example, exposed ends of the optical fibers 210), and the inner band 204, which creates an orifice that provides an entrance to the guidewire lumen 202. The energy emitted by the optical fibers 210 cuts, separates, and/or ablates the scar tissue, plaque build-up, calcium deposits and other types of undesirable lesion or bodily material within the subject's vascular system in a pattern substantially similar to that of the cross sectional configuration of the optical fibers 210.

As the energy emitted by the optical fibers 210 contacts the undesirable bodily material within the subject's vascular system, it separates and cuts such material in a generally concentric configuration. In other words, one of ordinary skill in the art may refer to this technique as coring. If the bodily material that is cut is substantially solid, it will appear as generally cylindrically looking core or plug. Although FIGS. 2-4 illustrate the optical fibers 210 in a generally concentric configuration, those skilled in the art will appreciate that there are numerous other ways and configurations in which to arrange a plurality of optical fibers 210. Additionally, although these two figures illustrate an outer jacket 206 and an inner band 204, those of skill in the art will appreciate that distinct components need not be used, and the optical fibers may be encapsulated within a single sleeve having a lumen. Accordingly, FIGS. 2-4 are not intended to represent the only way that a laser catheter may be configured and constructed, and all such configurations and constructions are within the knowledge of one skilled in the art are considered within the scope of the present disclosure.

In some embodiments, a laser ablation system may include multiple laser catheters 200 of different sizes (for example, external diameters) or structural configurations.

Examples of laser generators in accordance with the present disclosure include those available from The Spectranetics Corporation under the tradename CVX-300®. Further examples of laser generators in accordance with the present disclosure include those disclosed in U.S. Pat. Nos. 5,267,993, 5,383,199, and co-pending application U.S. patent application Ser. No. 13/804,812, the entireties of which are incorporated by reference herein for all purposes. Each of the above laser generators includes a fiber optic coupler for detachably coupling to a laser catheter, such as one or more of the laser catheters described herein, to deliver laser energy to a desired target (for example, a portion of the vasculature including a stenosis formed by scar tissue, plaque build-up, calcium deposits and/or other types of undesirable lesion) via the laser catheter. As such, the above laser generators facilitate coronary intervention or catheterization such as recanalizing occluded arteries, changing lesion morphology, and facilitating stent placement.

In some embodiments, the laser ablation system is configured to emit laser energy at wavelengths of between 300 nanometers to 350 nanometers, at pulse durations between 100 nanoseconds to 150 nanoseconds, and/or at frequencies between 1 pulse per second to 250 pulses per second. In some cases, the laser ablation system is configured to emit laser energy at wavelengths of about 308 nanometers (that is, within 5 percent of 308 nanometers), at pulse durations between 120 nanoseconds and 140 nanoseconds, and/or at frequencies between 25 pulses per second to 80 pulses per second.

Figure 5:
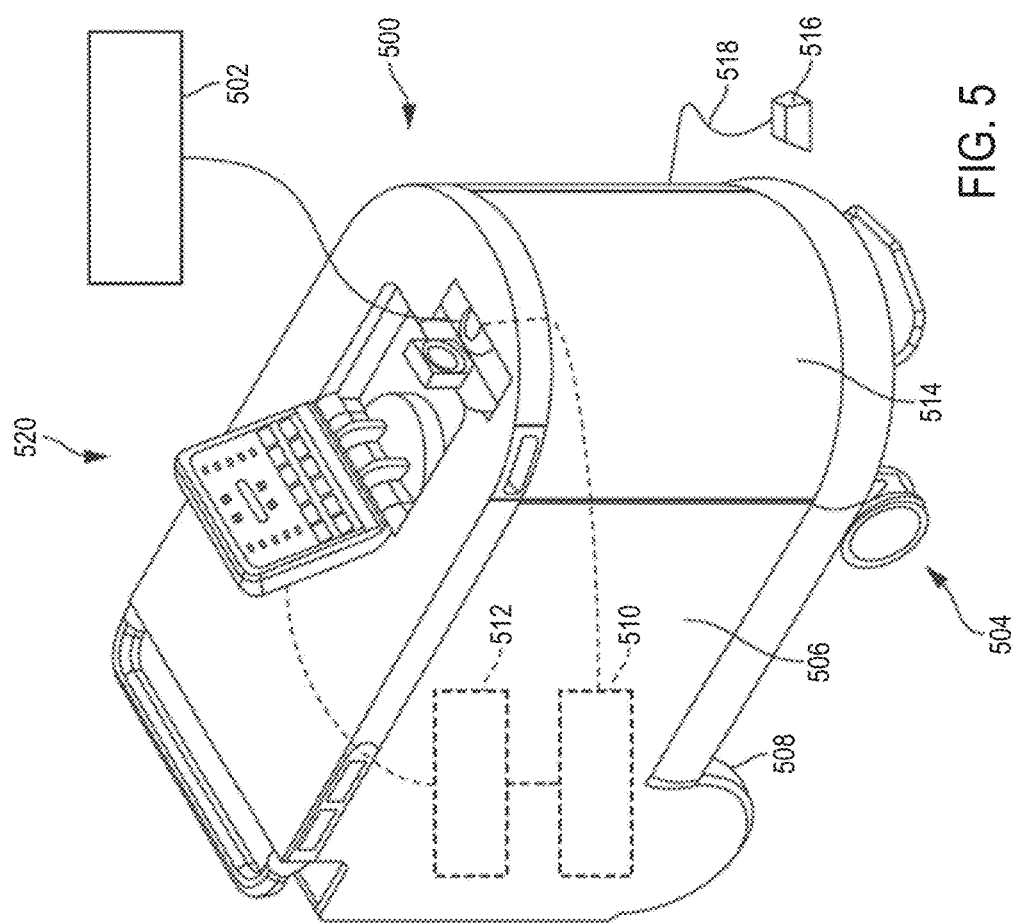
FIG. 5 is a schematic view of an exemplary embodiment of a laser ablation system in accordance with the present disclosure.

Referring now to FIG. 5, an exemplary embodiment of a laser ablation system 500 in accordance with the present disclosure is illustrated. The laser ablation system 500 includes a laser catheter 502, such as any of the laser catheters described herein, that detachably couples to and receives laser energy from a laser generator 504. The laser generator 504 includes a housing 506 that is supported by a plurality of wheels 508. The housing 506 houses a laser 510 and a controller 512. The housing 506 further includes a door 514 that provides access to a storage compartment.

A switch unit 516 (for example, a foot switch) may be stored in the storage compartment when not in use. The switch unit 516 may be actuated by an operator (for example, a clinician) to cause the laser 510 to generate laser energy. The switch unit 516 is coupled to the housing 506 via a tether 518. In some embodiments, the tether 518 may include power and/or communication cables (not illustrated) that facilitate power transmission and/or communication between the controller 512 and the switch unit 516. In other embodiments, the tether 518 may lack power and communication cables, and the controller 512 and the switch unit 516 may communicate via wireless signals.

The laser generator 504 further includes a control panel 520 carried on the housing 506. Via the control panel 520 an operator (for example, a clinician) is able to activate and control the operation of the laser 510 through the controller 512. Specifically, the controller 512 controls the operation of the laser 510 based on an indication of the state of the switch unit 516 (that is, actuated or not actuated). In addition, via the control panel 520 the operator may be able to modify operating parameters of the laser 510 through the controller 512.

Returning now to FIG. 1, the method continues at block 104 by positioning the laser ablation system in an appropriate position for treating the target. In some embodiments, positioning the laser system in an appropriate position includes positioning the distal end of a laser catheter within the vasculature of a subject proximate a target to be treated. In some embodiments, positioning the distal end of the laser catheter within the vasculature of the subject proximate the target includes positioning a guidewire in the vasculature of the subject, crossing a stenosis at the target with the guidewire, and advancing the laser catheter along the guidewire such that the distal end of the laser catheter is proximate the target.

The method continues at block 106 by activating the laser ablation system to deliver laser energy to and thereby treat the target. In some embodiments, activating the laser ablation system to deliver laser energy includes activating the laser generator to deliver laser energy to the laser catheter and emitting the laser energy from the distal end of the laser catheter to deliver laser energy to and thereby ablate a stenosis at the target. In some embodiments and as described above, the laser energy emitted from the laser catheter may separate and cut the thrombus in a generally concentric configuration (that is, core the tissue) depending on the configuration of the optical fibers carried by the laser catheter. In some embodiments, emitting the laser energy from the distal end of the laser catheter to ablate the stenosis includes varying the intensity of the emitted laser energy. In some embodiments, emitting the laser energy from the distal end of the laser catheter to ablate the stenosis includes varying the repetition rate of the emitted laser energy.

The method continues at block 108 by withdrawing the laser ablation system from the subject. In some embodiments, withdrawing the laser ablation system from the subject includes removing the laser catheter from the vasculature of the subject.

In some embodiments, the method may include employing multiple laser catheters having different sizes or configurations. For example, the method may include uncoupling a first laser catheter (for example, a laser catheter having a first size) from the laser generator, coupling a second laser catheter (for example, a laser catheter having a second size, the second size being different than the first size) to the laser generator, positioning the distal end of the second laser catheter within the vasculature of a subject proximate the target, and emitting laser energy from the distal end of the second laser catheter to deliver laser energy to and thereby ablate the stenosis at the target.

At block 110, the method continues by providing a balloon system. Generally and in some embodiments, the balloon system includes a drug-coated balloon (DCB) catheter, which is described in more detail below. The DCB catheter is inserted into and delivers one or more therapeutic agents to the vasculature of a subject. In some embodiments, the balloon system also includes an inflation fluid source that delivers an inflation fluid to the DCB catheter to cause the balloon of the DCB catheter to inflate or expand and, in some embodiments, deliver the therapeutic agent(s) to the vasculature.

Examples of DCB catheters in accordance with the present disclosure include those available from Lutonix, Inc. of New Hope, Minn. under the tradename Lutonix®, such as the Lutonix® 014 catheter, and those available from Medtronic of Minneapolis, Minn., such as the IN.PACT® Admiral® catheter. Further examples of DCB catheters, therapeutic agents, and balloon coatings including therapeutic agents in accordance with the present disclosure include those disclosed in U.S. Pat. Nos. 8,114,429; 8,128,951; 8,257,304; 8,257,722; 8,491,925; 8,563,023; 8,673,332; 8,734,825, 8,740,841; 9,011,896; U.S. Pat. Apps. 62/098, 242; Ser. Nos. 13/628,608; 13/707,401; 11/411,635; 60/680, 450; 13/310,320; 12/712,134; 12/558,420; 12/210,344; 14/149,862; 13/560,538; 13/926,515; 61/665,758; 13/628, 627; 13/975,209; 13/975,220; 13/975,228; 14/032,336; 14/162,900; 14/254,160; 14/731,715; the entireties of which are incorporated by reference herein for all purposes.

Referring now to FIG. 6, an exemplary embodiment of a balloon system 600 in accordance with the present disclosure is illustrated. The balloon system 600 includes a DCB catheter 602 that receives inflation fluid from an inflation fluid source 604. The DCB catheter 602 includes a tubular element 606 that carries a drug-coated expandable element or balloon 608. The tubular element 606 includes an inflation lumen (not illustrated) that receives inflation fluid from the inflation fluid source 604 and delivers the inflation fluid to the balloon 608 to inflate the balloon 608. In some embodiments, the tubular element 606 also includes a guidewire lumen (not illustrated) for receiving a guidewire (not illustrated) to guide the DCB catheter 602 to the target.

The balloon 608 carries a coating 610 that includes one or more therapeutic agents. Therapeutic agents in accordance with the present disclosure can be chosen based upon functional characteristics, including, but not necessarily limited to, the ability to inhibit restenosis, mitosis or cellular proliferation. For example, a therapeutic agent can be a taxane, including paclitaxel, docetaxel, protaxel, DHA-paclitaxel, PG-paclitaxel, docosahexaenoic acid (DHA), or any combinations or derivatives thereof capable of inhibiting mitosis or cellular proliferation. In some cases, the presence of a mitotic inhibitor prevents restenosis that may occur in the absence of the inhibitor. Other examples of therapeutic agents include rapamycin (for example, sirolimus) or a derivative of rapamycin (for example, everolimus), or any combinations or derivatives thereof. Additionally or alternatively, specific inhibitors of neovascularization such as thalidomide, statins such as atorvastatin, cerivastatin, fluvastatin, or anti-inflammatory drugs like corticoids or lipophilic derivatives of corticoids such as betamethasone diproprionate or dexa-methasone-21-palmitate are examples of oxitherapeutic agents that can be used in accordance with the present disclosure. In some cases, the therapeutic agent is stable against oxidative degradation, or oxidation in sensitive. Various therapeutic agents may be applied or combined if different pharmacological actions are required or efficacy or tolerance is to be improved.

Coatings in accordance with the present disclosure include a therapeutic agent dispersed throughout a polymer matrix. The polymer coating may include additional components such as a plasticizer and/or wax. The therapeutic agent can be either water-soluble or water-insoluble. The polymer matrix may be complexed with iodine, or non-covalently bound iodine may be dispersed throughout the polymer matrix. In some embodiments, the polymer matrix is a non-ionic thermoplastic polymer or co-polymer. In some embodiments, the amphiphilic polymer is hydroxypropyl cellulose (HPC), polyvinyl pyrrolidone (PVP), polyethylene glycol (PEG), methyl cellulose, hydroxypropyl methylcellulose, or co-polymers of N-vinylpyrrolidone with other reactive double bond containing monomers such as styrene, acrylic acid, vinyl acetate or vinyl caprolactam. PVP and HPC exhibit higher solubility rates in aqueous solvents than PEG. Molecular weight of the polymers may also factor into solubility rates. In some embodiments, the PEG has as molecular weight of 1.5 KD to 50 KD. Co-polymers can be block or random.

Coatings in accordance with the present disclosure include an amphiphilic polymer coating that includes one or more therapeutic agents and one or more amphiphilic polymers or co-polymers. The amphiphilic polymer coating may include additional components such as a plasticizer and/or wax. The therapeutic agent can be either water-soluble or water-insoluble. Hydration of the amphiphilic polymer coating occurs immediately when exposed to aqueous fluids, such as blood in vivo, causing the amphiphilic polymer coating to dissolve and the therapeutic agent to release into tissue of the vasculature of the subject. Thus, the amphiphilic polymer coating is bioerodable in the sense that it is removable by bodily fluids, and non-durable. In some embodiments, the amphiphilic polymer or co-polymer is a non-ionic thermoplastic polymer or co-polymer. In some embodiments, the amphiphilic polymer is hydroxypropyl cellulose (HPC), polyvinyl pyrrolidone (PVP), polyethylene glycol (PEG), methyl cellulose, hydroxypropyl methylcellulose, or co-polymers of N-vinylpyrrolidone with other reactive double bond containing monomers such as styrene, acrylic acid, vinyl acetate or vinyl caprolactam. PVP and HPC exhibit higher solubility rates in aqueous solvents than PEG. Molecular weight of the polymers may also factor into solubility rates. In some embodiments, the PEG has as molecular weight of 1.5 KD to 50 KD. In some embodiments, the coating includes paclitaxel in PEG complexed with iodine in a polymer matrix, or non-covalently bound iodine may be dispersed throughout the polymer matrix. The PEG has a number average molecular weight, Mn, of about 8 KD. The amphiphilic polymer may also be a poly(hydroxyethyl methacrylic) acid, also known as poly(HEMA). In some embodiments, the poly(HEMA) has a number average molecular weight, Mn, below approximately 8 KD. In some embodiments, the poly(HEMA) has a number average molecular weight, Mn, of approximately 7 KD. In some embodiments, the amphiphilic polymer may be a co-polymer of HEMA with a monomer such as glycidyl methacrylate (GMA) or acrylic acid. Co-polymers can be block or random.

Coatings in accordance with the present disclosure may include a therapeutic agent combined with various adjuvants and excipients to enhance efficacy or delivery of the therapeutic agents. For example, the therapeutic agents can be combined with lipophilic antioxidant such as nordihydroguaiaretic acid, resveratrol, propyl gallate, hydroxytoluene, butylated hydroxyanisole, and ascorbyl palmitate to enhance the adhesion of the therapeutic to the balloon 608. In some embodiments, the combination of a therapeutic agent such as paclitaxel and a lipophilic antioxidant such as nordihydroguaiaretic acid can be applied to the balloon 608 without the need for additional polymers.

Coatings in accordance with the present disclosure may be applied to balloons by using a variety of processes. For example, coatings may be applied to balloons using similar processes to the following Examples regarding coating of PET and Nylon 12 coupons. Solution percentages provided are by weight.

Example 1

One (1.0) grams of a 7.5 percent solution of 60 K Dalton HPC in ethanol is mixed with 0.15 grams of 1 percent solution of propylene glycol (plasticizer) in acetone, 0.075 grams paclitaxel and 0.08 grams n-butanol. The mixture is heated in a water bath to dissolve the paclitaxel; a clear solution results. When dip coated (single dip) on PET coupons at a dip speed of about 10 inches/minute, and dried at room temperature, there results a slightly milky dry coating. About 3 $cm^2$ of coupon surface is coated per coupon. The average coating density determined by gravimetric analysis is 6 $\mu g/mm^2$ and the implied paclitaxel density is 3 $\mu g/mm^2$. The dry coating is sufficiently ductile to withstand a 180 degree bend without cracking or delaminating. A coupon coated as above is immersed in 3 ml of 37 degrees C. water for 3 minutes with agitation, after which the coupon is removed and the turbid suspension diluted with 9 ml dimethyl sulfoxide (DMSO) to produce a clear solution. Quantitative UV analysis at 260 nm and 280 nm vs. a standard curve shows an 88 percent recovery. This result demonstrates the rapid dissolution of the amphiphilic polymer coating and drug release in vitro. The in vivo milieu is expected to present serum proteins with a surfactant effect, which will increase the dissolution rate of the drug and coating polymer in vivo.

Example 2

0.075 grams paclitaxel is mixed with 0.9 grams of a 20 percent povidone-iodine solution in 2-propanol, 0.06 grams of a 10 percent propylene glycol solution in 2-propanol and 0.04 grams acetone. When dip coated (single dip) on a PET coupon at a dip speed of 10 inches/min, and dried at room temperature, there results a clear amber dry coating. About 2.5 $\mu g/mm^2$ of paclitaxel is deposited. The above coupon is immersed in 1.5 ml of 37 degrees C. water for 30 seconds. All of the coating dissolves in the water, and the solution is totally transparent amber, and not turbid as in Example 1.

Example 3

An identical formula to Example 2 is made, however noniodinated PVP is employed instead of povidone-iodine of the same molecular weight (40 K Dalton). When dip coated (single dip) on a PET coupon at a dip speed of 10 inches/min, and dried at room temperature, there results a clear water white dry coating. About 2.5 $\mu g/mm^2$ of paclitaxel is deposited. This coupon is immersed in 1.5 ml of 37 degrees C. water for 30 seconds. All of the coating polymer dissolves in the water, and the solution shows a suspension of needle crystals. This suspension becomes more turbid after 24 hours, while the above amber solution from Example 2 remains transparent. This demonstrates that the povidone-iodine changes the aqueous solubility of paclitaxel.

Example 4

0.1 grams rapamycin (available from LC Laboratories of Woburn, Mass.) is dissolved in 0.08 grams of a 10 percent propylene glycol solution in 2-propanol and 0.053 grams acetone at 40 degrees C. The solution is cooled to room temperature, then added to 1.2 grams of a 20 percent solution of povidone-iodine in 2-propanol. The formula is dip coated (single dip) on a Nylon 12 coupon, and dried at room temperature for 30 minutes. The coupon is immersed in 1 ml of 37 degrees C. water for one minute. All of the coating dissolves in the water, and the solution is clear amber.

Example 5

An identical formula to Example 4 is made, however noniodinated C-30 PVP is employed instead of povidone-iodine. The formula is dip coated (single dip) on a Nylon 12 coupon, and dried at room temperature for 30 minutes. The coupon is immersed in 1 ml of 37 degrees C. water for one minute. All of the coating dissolves in the water, and the solution is turbid due to the water-insoluble rapamycin.

Example 6

0.1 grams everolimus (available from LC Laboratories) is dissolved in 0.08 grams of a 10 percent propylene glycol solution in 2-propanol and 0.053 grams acetone at 40 degrees C. The solution is cooled to room temperature, then added to 1.2 grams of a 20 percent solution of povidone-iodine in 2-propanol. The formula is dip coated (single dip) on a Nylon 12 coupon, and dried at room temperature for 30 minutes. The above coupon is immersed in 1 ml of 37 degrees C. water for one minute. All of the coating dissolves in the water, and the solution is clear amber.

Example 7

An identical formula to Example 6 is made, however noniodinated C-30 PVP is employed instead of povidone-iodine. The formula is dip coated (single dip) on a Nylon 12 coupon, and dried at room temperature for 30 minutes. The above coupon is immersed in 1 ml of 37 degrees C. water for one minute. All of the coating dissolves in the water, and the solution is turbid due to the water-insoluble everolimus.

Light scattering experiments at 600 nm and 700 nm were performed comparing the drug (paclitaxel, rapamycin and everolimus) and polymer eluted water solutions of Examples 2, 4 and 6 (containing povidone-iodine) with Examples 3, 5 and 7 (containing non-iodinated PVP). The results illustrated in Table I below provide a quite unexpected increase in solubility of paclitaxel, rapamycin and everolimus in the povidoneiodine eluted water solutions of Examples 2, 4 and 6 compared to the non-iodinated PVP eluted water solution of Examples 3, 5 and 7. Consequently, and quite unexpectedly this suggests that the iodine complexed PVP polymer may assist in tissue uptake of the non-aqueous soluble therapeutic agents in vivo.

TABLE I

Optical density measurements

| Example | Therapeutic Agent | Wave-length | Polymer | Optical Density | Solubility Increase |
|---|---|---|---|---|---|
| 2 | paclitaxel | 600 nm | PVP-iodinated | 0.120 | 2.99 |
| 3 | paclitaxel | 600 nm | PVP (ton-iodinated) | 0.359 | — |
| 4 | rapamycin | 600 nm | PVP-iodinated | 0.079 | 3.10 |
| 5 | rapamycin | 600 nm | PVP (non-iodinated) | 0.245 | — |
| 6 | everolimus | 600 nm | PVP-iodinaied | 0.068 | 2.38 |

TABLE I-continued

Optical density measurements

| Example | Therapeutic Agent | Wave-length | Polymer | Optical Density | Solubility Increase |
|---|---|---|---|---|---|
| 7 | everolimus | 600 nm | PVP (non-iodinated) | 0.162 | — |
| 2 | paclitaxel | 700 nm | PVP-iodinated | 0.089 | 3.19 |
| 3 | paclitaxel | 700 nm | PVP (non-iodinated) | 0.284 | — |
| 4 | rapamycin | 700 nm | PVP-iodinated | 0.056 | 3.66 |
| 5 | rapamycin | 700 nm | PVP (non-iodinated) | 0.205 | — |
| 6 | everolimus | 700 nm | PVP-iodinated | 0.051 | 2.66 |
| 7 | everolimus | 700 nm | PVP (non-iodinated) | 0.136 | — |

Example 8

0.2 grams of iodine (Sigma-Aldrich) was added to 10 grams of methanol and dissolved with heat and agitation. 4.29 grams of PEG (4 K Daltons, Fluka) was then added, and dissolved with mild heat and agitation. 0.20 grams of paclitaxel was added to 1.66 grams of the above PEG-iodine solution. Mild heat and agitation were used to dissolve the paclitaxel. A Nylon 12 coupon was coated with the formulation and dried for about 1 hour. The coupon was then soaked in 1.5 ml bovine serum at 37 degrees C. for 3 minutes. 200 micro-liters of the serum sample was tested for optical density at 600 and 700 nm on a plate reader.

Example 9

An identical formula to Example 8 is made without iodine as a counter example. A Nylon 12 coupon was coated with the formulation and dried for about 1 hour. The coupon was then soaked in 1.5 ml bovine serum at 37 degrees C. for 3 minutes. 200 micro-liters of the serum sample was tested for optical density at 600 and 700 nm on a plate reader.

Light scattering experiments at 600 nm and 700 nm were performed comparing the drug (paclitaxel) and polymer eluted bovine serum solutions of Example 8 (iodinated PEG) with Example 9 (non-iodinated PEG). The results illustrated in Table II below provide a quite unexpected increase in solubility of paclitaxel in the PEG eluted bovine serum solution of Example 8 compared to the non-iodinated PEG eluted bovine serum solution of Example 9. Consequently, and quite unexpectedly this suggests that the iodine complexed PEG polymer may assist in tissue uptake of the non-aqueous soluble therapeutic agents in vivo.

TABLE II

Optical density measure Merits

| Example | Therapeutic Agent | Wave-length | Polymer | Optical Density | Solubility Increase |
|---|---|---|---|---|---|
| Serum blank | — | 600 nm | — | 0.099 | — |
| 8 | paclitaxel | 600 nm | poly-4KD-iodinated | 0.109 | 1.13 |
| 9 | paclitaxel | 600 nm | poly-4KD-(non-iodinated) | 0.123 | — |
| Serum blank | — | 700 nm | — | 0.062 | — |
| 8 | paclitaxel | 700 nm | poly-4KD-iodinated | 0.069 | 1.26 |
| 9 | paclitaxel | 700 nm | poly-4KD-(non-iodinated) | 0.087 | — |

Example 10

A morphaline based initiator (ME-Br) was synthesized according to the following procedure. 18 ml 4-(2-hydroxyethyl) morpholine was dissolved in 200 ml toluene. 21.2 ml triethylamine (dried over Na2S04) was added. The mixture was cooled in an ice bath. With stirring, 18.36 ml 2-bromoisobutyryl bromide was added dropwise over 30 minutes. The mixture was stirred in a cooling bath for an additional hour and then room temperature for 40 hours. The precipitated triethylarnmonium salt was filtered off and washed with 50 ml toluene. The solvent was rotoevaporated from the combined solution. The product, a brownish oil, was analyzed by NMR and was found to be highly pure. It was used without further purification. A 10 KD polymer was synthesized according to the following ATRP procedure utilizing the ME-Br initiator. 4.076 grams of the above ME-Br initiator was loaded in a 100 ml round bottomed flask, equipped with a stir bar. A solution of 0.0280 grams tris[(2-pyridyl)methyl]amine (TPMA), 0.0215 CuBr2 and 0.0795 grams azobisisobutyronitrile (AIBN) in 100 ml ethanol was prepared and added. To this solution, 100 ml HEMA was added, the flask was capped, cooled in an ice bath and purged with nitrogen for 2 hours. The reaction was then carried out at 60 degrees C. for 3 hours. 30 percent conversion was achieved. The polymer was precipitated in ether, washed with ether and dried. Molecular weight by GPC was 10,000 grams per mole. The 10 KD material was found to be water insoluble.

Example 11

A morphaline based initiator (ME-Br) was synthesized according to the procedure described in Example 10. A 7 KD polymer was synthesized according to the following procedure. 12.24 grams of the above ME-Br initiator was loaded in a 100 ml round bottomed flask, equipped with a stir bar. A solution of 0.0280 grams tris[(2-pyridyl)methyl]amine (TPMA), 0.0215 CuBr2 and 0.0795 grams azobisisobutyronitrile (AIBN) in 100 ml ethanol was prepared and added. To this solution, 100 ml HEMA was added, the flask was capped, cooled in an ice bath and purged with nitrogen for 2 hours. The reaction was then carried out at 60 degrees C. for 2 hours. 32 percent conversion was achieved. The polymer was precipitated in ether, washed with ether, re-dissolved in methanol, re-precipitated in ether and dried. Molecular weight by GPC was 7,000 grams per mole. The 7 KD material was found to have water solubility.

Example 12

A 30 percent solution of 7 KD poly(HEMA) in 2-propanol was prepared in accordance with the procedures of Example 11. To 0.79 grams of this solution was added: 0.12 grams of 10 percent propylene glycol in 2-propanol, 0.06 grams acetone and 0.1 grams paclitaxel. Gentle heating was used to form a clear solution. This paclitaxel containing solution was used to dip coat onto Nylon 12 coupons. The coupons were dried at room temperature. The resultant coating was clear and free of obvious phase separation.

Example 13

A 30 percent solution of 7 KD poly(HEMA) in 2-propanol was prepared in accordance with the procedures of Example 11 with the addition of iodine at a level of 7 percent iodine based on poly(HEMA). A clear amber solution resulted. To 0.79 grams of this solution was added: 0.12 grams of 10 percent propylene glycol in 2-propanol, 0.06 grams acetone and 0.1 grams paclitaxel. Gentle heating was used to form an amber solution. This paclitaxel containing solution was used to dip coat onto Nylon 12 coupons. The coupons were dried at room temperature. The resultant coating was clear amber and free of obvious phase separation.

The coupons from Examples 12 and 13 were then immersed and agitated in 1.5 ml of adult bovine serum at 37 degrees C. for 3 minutes. Subsequent gravimetric analysis showed that 90 percent of both coatings were removed by this process. 200 micro-liters of the serum samples were tested for optical density at 600 and 700 nm on a plate reader. The results are provided in Table III below, show an increase in solubility of paclitaxel in the iodinated poly (HEMA) eluted bovine serum solution of Example 13 compared to the non-iodinated poly(HEMA) eluted bovine serum solution of Example 12. Consequently, this suggests that iodine enhances the solubility of hydrophobic materials contained in the coating when in contact with biological systems. The data in Table III also indicates that poly (HEMA) synthesized using the ATRP initiator (ME-Br) forms a fully amphiphilic coating that achieves water solubility, and consequent rapid release of the drug; that poly (HEMA) is capable of complexing with iodine, resulting in improved solubility of a substantially water-insoluble, hydrophobic drug such as paclitaxel; that poly(HEMA) synthesized using the ATRP initiator (ME-Br) is useful as a medical device coating for rapid release of drug agents into tissue; and the addition of iodine to poly(HEMA) may enhance solubility and tissue uptake of a substantially water insoluble, hydrophobic drug such as paclitaxel.

TABLE III

| | | Optical density measure Merits | | | |
|---|---|---|---|---|---|
| Example | Therapeutic Agent | Wavelength | Polymer | Optical Density | Solubility Increase |
| Serum blank | — | 600 nm | — | 0.144 | — |
| 11 | paclitaxel | 600 nm | poly(HEMA)-7KD-iodinated | 0.150 | 1.09 |
| 10 | paclitaxel | 600 nm | poly(HEMA)- 7 KD (non-iodinated) | 0.163 | — |
| Serum blank | — | 700 nm | — | 0.102 | — |
| 11 | paclitaxel | 700 nm | poly(HEMA)-7KD-iodinated | 0.107 | 1.10 |
| 10 | paclitaxel | 700 nm | poly(HEMA)- 7 KD (non-iodinated) | 0.118 | — |

In some embodiments, the DCB catheter 620 further includes a protective sheath 612 that is translatable relative to the tubular element 606 and the balloon 608. The protective sheath 612 initially surrounds the unexpanded balloon 608 to prevent the coating 610 from prematurely dissolving when the DCB catheter 620 is inserted into the vasculature of the subject.

Figure 7B:
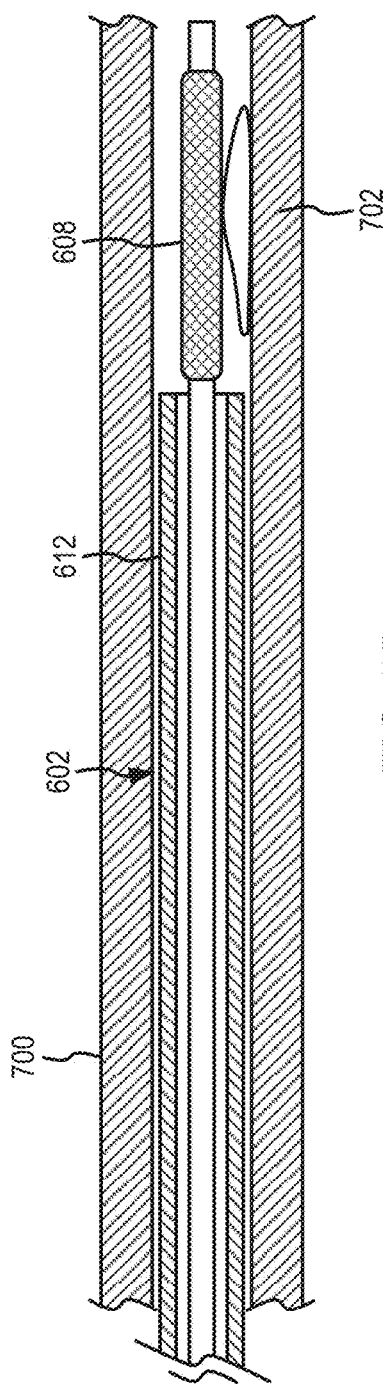
FIG. 7B is an elevation longitudinal section view of the balloon catheter of FIG. 6; the balloon is in a distally advanced position relative to the protective sheath and is longitudinally aligned with the target and radially offset from the target.
Figure 7C:
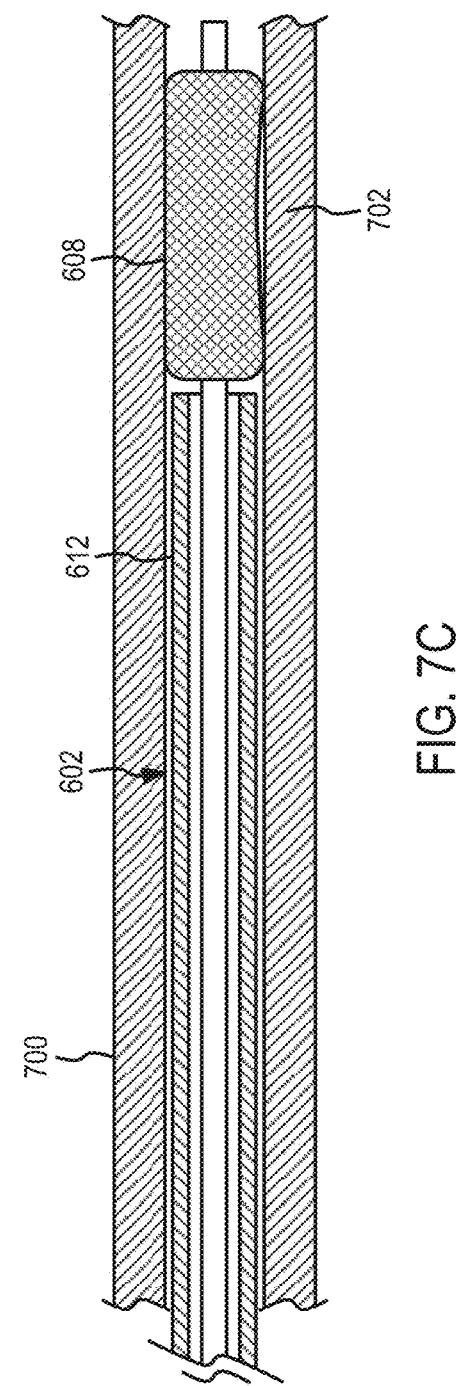
FIG. 7C is an elevation longitudinal section view of the balloon catheter of FIG. 6; the balloon is in the distally advanced position relative to the protective sheath and is longitudinally aligned with the target and radially expanded to engage the target.

Returning now to FIG. 1 and referring also to FIGS. 7A-7C, the method continues at block 112 by positioning the balloon system in an appropriate position for delivering the therapeutic agent(s) to the vasculature of the subject. In some embodiments, positioning the balloon system in an appropriate position includes (1) as illustrated in FIG. 7A, positioning the DCB catheter 602 in the vasculature 700 of the subject such that the catheter 602 is longitudinally offset (that is, offset in a longitudinal direction of the catheter 602) from the target 702 to be treated (for example, the portion of the vasculature that previously included the stenosis treated by the laser ablation system or that includes any remnants of the stenosis treated by the laser ablation system); the balloon 608 may be in an unexpanded configuration and a proximally retracted position within the protective sheath 612; (2) as illustrated in FIG. 7B, translating the balloon 608 to a distally advanced position relative to the protective sheath 612 such that the balloon 608 is longitudinally aligned with the target 702 and radially offset (that is, offset in a radial direction of the catheter 602) from the target 702; and (3) as illustrated in FIG. 7C, expanding the balloon 608 in the radial direction to contact the target 702. In some embodiments, the inflation fluid source 604 delivers inflation fluid to the balloon 608 to expand the balloon 608. At block 614, the balloon 608 delivers the therapeutic agent(s) to the target 702. In some embodiments, the balloon 608 delivers the therapeutic agent(s) to the target 702 by the balloon 608 contacting the blood of the subject, thereby dissolving the coating 610, and/or expanding the balloon 608 to contact the target 702.

In some embodiments, the coating 610 includes a therapeutic agent that is a restenosis inhibitor (such as paclitaxel) to inhibit restenosis at the target. In some embodiments and if the target includes any remnants of the stenosis treated by the laser ablation system, expanding the balloon 608 may also facilitate angioplasty at the target.

The method concludes at block 116 by withdrawing the balloon system from the subject. In some embodiments, withdrawing the balloon system from the subject includes removing the DCB catheter 602 from the vasculature 700 of the subject.

Animal Study I.

An in-stent restenosis model in the carotid artery of hypercholesterolemic rabbits was established to create chronic total occlusion for assessment of laser ablation with adjunct treatment with a drug-coated balloon system.

The animals (rabbits) were fed a 1 percent high cholesterol diet with subsequent 3F Fogarty injury and bare metal stent implantation after seven days. The atherogenic high cholesterol feed was continued until day 28 at which time the diet was switched to 0.025 percent cholesterol for the remaining in-life-period. An intra-luminal bovine thrombin injection within the restenotic stented arterial segment was performed at ~62 days after initiation of the high cholesterol diet) to create total occlusion. Surviving animals 30 days later underwent: i) laser ablation and treatment with a drug-coated balloon (DCB) or ii) balloon angioplasty (PTCA) and DCB, and were then studied/terminated at 28-day follow-up.

Materials and Methods

Animals Treated with Laser Ablation and Drug-Coated Balloon Systems

Laser ablation of carotid stents with occlusive lesions was performed using a CVX-300-P® Excimer Laser System [Spectranetics, Colorado Springs, Colo.] followed by drug-coated balloon treatment for animals 1-4 as described below. Anti-platelet therapy (aspirin ~40 mg PO) was administered for the remainder of the study, which was a 28-days period following laser ablation. Heparin (150 IU/kg) was given during the catheterization procedure.

Animal 1

The animal was treated under fluoroscopy to provide images of the vasculature and positions of medical devices in the vasculature. The stenosis was crossed with a guidewire. The stenosis partially occluded the vasculature, and pre-treatment optical coherence tomography (OCT) was used to provide images of the vasculature and the stenosis. A 0.9 mm diameter Turbo-Elite™ laser catheter was then used as follows:

(1) one laser ablation pass through the stent to a position distal to the stent at a fluence of 30 mJ/mm$^2$ and a repetition rate of 30 Hz;
(2) laser ablation at a position proximal to the stent at a fluence of 30 mJ/mm$^2$ and a repetition rate of 30 Hz;
(3) one laser ablation pass in the stent at a fluence of 60 mJ/mm$^2$ and a repetition rate of 80 Hz;
(4) laser ablation at a position distal to the stent at a fluence of 30 mJ/mm$^2$ and a repetition rate of 30 Hz;
(5) laser ablation at a position proximal to the stent at a fluence of 30 mJ/mm$^2$ and a repetition rate of 30 Hz; and
(6) one laser ablation pass in the stent at a fluence of 60 mJ/mm$^2$ and a repetition rate of 80 Hz.

A 1.4 mm diameter Turbo-Elite™ laser catheter was then used as follows:

(1) one laser ablation pass from a position proximal to the stent, through the stent, and to a position distal to the stent at a fluence of 30 mJ/mm$^2$ and a repetition rate of 30 Hz;
(2) laser ablation at a position proximal to the stent at a fluence of 30 mJ/mm$^2$ and a repetition rate of 30 Hz; and
(3) two laser ablation passes in the stent at a fluence of 50 mJ/mm$^2$ and a repetition rate of 50 Hz.

OCT was then used to provide images of the vasculature. A 3.0×15 mm Lutonix® 014 balloon catheter was then inflated in the stent at a pressure of 6 atm for 60 seconds.

Animal 2

The animal was treated under fluoroscopy to provide images of the vasculature and positions of medical devices in the vasculature. The stenosis was crossed with a guidewire. The stenosis partially occluded the vasculature, and pre-treatment OCT was used to provide images of the vasculature and the stenosis. A 0.9 mm diameter Turbo-Elite™ laser catheter was then used as follows:

(1) one laser ablation pass from a position proximal to the stent, through the stent, and to a position distal to the stent at a fluence of 30 mJ/mm$^2$ and a repetition rate of 30 Hz; and
(2) one laser ablation pass in the stent at a fluence of 60 mJ/mm$^2$ and a repetition rate of 80 Hz.

A 1.4 mm diameter Turbo-Elite™ laser catheter was then used as follows:

(1) one laser ablation pass from a position proximal to the stent, through the stent, and to a position distal to the stent at a fluence of 30 mJ/mm$^2$ and a repetition rate of 30 Hz; and
(2) one laser ablation pass in the stent at a fluence of 50 mJ/mm$^2$ and a repetition rate of 50 Hz.

OCT was then used to provide images of the vasculature. A 3.0×15 mm Lutonix® 014 balloon catheter was then inflated in the stent at a pressure of 6 atm for 60 seconds.

Animal 3

The animal was treated under fluoroscopy to provide images of the vasculature and positions of medical devices in the vasculature. The stenosis was crossed with a guidewire. The stenosis partially occluded the vasculature, and pre-treatment OCT was used to provide images of the vasculature and the stenosis. A 0.9 mm diameter Turbo-Elite™ laser catheter was then used as follows:

(1) two laser ablation passes from a position proximal to the stent and through the stent at a fluence of 30 mJ/mm$^2$ and a repetition rate of 30 Hz; and
(2) one laser ablation pass in the stent at a fluence of 60 mJ/mm$^2$ and a repetition rate of 80 Hz.

A 1.4 mm diameter Turbo-Elite™ laser catheter was then used as follows:
(1) two laser ablation passes in the stent at a fluence of 30 mJ/mm$^2$ and a repetition rate of 30 Hz;
(2) one laser ablation pass in the stent at a fluence of 50 mJ/mm$^2$ and a repetition rate of 50 Hz;
(3) laser ablation at a position distal to the stent at a fluence of 30 mJ/mm$^2$ and a repetition rate of 30 Hz;
(4) one laser ablation pass in the stent at a fluence of 50 mJ/mm$^2$ and a repetition rate of 50 Hz; and
(5) one laser ablation pass in the stent at a fluence of 60 mJ/mm$^2$ and a repetition rate of 80 Hz.

0.5 mL of lidocaine and 0.25 mL of nitroglycerine was then administered to the vasculature. OCT was then used to provide images of the vasculature. A 3.0×15 mm Lutonix® 014 balloon catheter was then inflated in the stent at a pressure of 6 atm for 60 seconds. 0.5 mL of lidocaine and 0.25 mL of nitroglycerine was then administered to the vasculature.

Animal 4

The animal was treated under fluoroscopy to provide images of the vasculature and positions of medical devices in the vasculature. The stenosis was crossed with a guidewire by using a 0.014 inch guidewire-compatible Quick-Cross™ Capture™ guidewire retriever. The stenosis partially occluded the vasculature, and pre-treatment OCT was used to provide images of the vasculature and the stenosis. 0.5 mL of lidocaine and 0.25 mL of nitroglycerine was then administered to the vasculature. A 0.9 mm diameter Turbo-Elite™ laser catheter was then used as follows:
(1) laser ablation at a position proximal to the stent at a fluence of 30 mJ/mm$^2$ and a repetition rate of 30 Hz;
(2) one laser ablation pass in the stent at a fluence of 50 mJ/mm$^2$ and a repetition rate of 50 Hz;
(3) laser ablation at a position distal to the stent at a fluence of 30 mJ/mm$^2$ and a repetition rate of 30 Hz;
(4) one laser ablation pass from a position proximal to the stent, through the stent, and to a position distal to the stent at a fluence of 30 mJ/mm$^2$ and a repetition rate of 30 Hz; and
(5) one laser ablation pass in the stent at a fluence of 60 mJ/mm$^2$ and a repetition rate of 80 Hz.

The laser catheter contacted the stent, and an angioplasty balloon catheter was employed to urge the stent to expand toward the wall of the vasculature. Specifically, a 2.0×20 mm Maverick$^2$ Monorail™ balloon catheter (available from Boston Scientific Corporation) was inflated at the proximal end of the stent at a pressure of 8 atm for 60 seconds. A 1.4 mm diameter Turbo-Elite™ laser catheter was then used as follows:
(1) two laser ablation from a position proximal to the stent, through the stent, and to a position distal to the stent at a fluence of 30 mJ/mm$^2$ and a repetition rate of 30 Hz; and
(2) one laser ablation pass in the stent at a fluence of 50 mJ/mm$^2$ and a repetition rate of 50 Hz.

0.5 mL of lidocaine and 0.25 mL of nitroglycerine was then administered to the vasculature. The 1.4 mm diameter Turbo-Elite™ laser catheter was then used as follows:
(1) one laser ablation pass in the stent at a fluence of 50 mJ/mm$^2$ and a repetition rate of 50 Hz; and
(2) one laser ablation pass in the stent at a fluence of 60 mJ/mm$^2$ and a repetition rate of 80 Hz.

0.5 mL of lidocaine and 0.25 mL of nitroglycerine was then administered to the vasculature. The 2.0×20 mm Maverick$^2$ Monorail™ balloon catheter was used as follows:
(1) inflation at a position distal to the stent at a pressure of 6 atm for 60 seconds;
(2) inflation in the stent at a pressure of 9 atm for 60 seconds;
(3) inflation at a position proximal to the stent at a pressure of 8 atm for 60 seconds;
(4) inflation at a position proximal to the position in (3) at a pressure of 8 atm for 60 seconds;
(5) inflation at the position in (3) at a pressure of 9 atm for 60 seconds; and
(6) inflation in the stent at a pressure of 9 atm for 60 seconds.

OCT was then used to provide images of the vasculature. A 3.0×15 mm Lutonix® 014 balloon catheter was then used as follows:
(1) inflation in the stent at a pressure of 6 atm for 60 seconds; and
(2) inflation at the proximal end of the stent at a pressure of 1 atm for 60 seconds.

Animals Treated with Balloon Angioplasty and Drug-Coated Balloon Systems

Balloon angioplasty of carotid stents with occlusive lesions was performed followed by drug-coated balloon treatment for animals 5 and 6 as described below. Antiplatelet therapy (aspirin ~40 mg PO) was administered for the remainder of the study. Heparin (150 IU/kg) was given during the catheterization procedure.

Animal 5

The animal was treated under fluoroscopy to provide images of the vasculature and positions of medical devices in the vasculature. The stenosis was crossed with a guidewire. The stenosis fully occluded the vasculature, and pre-treatment OCT was not used. A 2.5×20 mm Maverick$^2$ Monorail™ balloon catheter was used as follows:
(1) inflation in the stent at a pressure of 6 atm for 60 seconds; and
(2) inflation at a position proximal to the stent at a pressure of 6 atm for 60 seconds.

A dissection proximal to the stent was revealed by fluoroscopy. Subsequent short inflations of the Maverick$^2$ Monorail™ balloon catheter were performed along proximal branch to improve flow. The dissection was still present. A 3.0×15 mm Lutonix® 014 balloon catheter was then inflated in the stent at a pressure of 6 atm for 60 seconds.

Animal 6

The animal was treated under fluoroscopy to provide images of the vasculature and positions of medical devices in the vasculature. The stenosis was crossed with a guidewire by using a 0.014 inch guidewire-compatible Quick-Cross™ Capture™ guidewire retriever. The stenosis fully occluded the vasculature, and pre-treatment OCT was not used. 0.5 mL of lidocaine and 0.25 mL of nitroglycerine was then administered to the vasculature. A 2.5×20 mm Maverick$^2$ Monorail™ balloon catheter was used as follows:
(1) two inflations at a position distal to the stent at a pressure of 6 atm for 60 seconds;
(2) two inflations at a distal portion of the stent at a pressure of 6 atm for 60 seconds;
(3) two inflations at an intermediate portion of the stent at a pressure of 6 atm for 60 seconds;
(4) two inflations at a proximal portion of the stent at a pressure of 6 atm for 60 seconds; and (5) two inflations at a position proximal to the stent at a pressure of 6 atm for 60 seconds.

A 3.0×15 mm Lutonix® 014 balloon catheter was then inflated in the stent at a pressure of 6 atm for 60 seconds.

Results

At the scheduled termination, the stented carotid was found patent in animals 1, 2, and 3, while persistent occlusions were noted for animals 4, 5, and 6. Carotid artery segments with stents were dehydrated in a graded series of ethanol and embedded in methylmethacrylate (MMA) resin. After polymerization, two to three millimeter length segments were sawed from the proximal, middle and distal portions of each stent. Histologic sections at 6-micron thickness were then prepared using a rotary microtome, mounted on charged glass slides, and stained with hematoxylin and eosin and Movat Pentachrome (connective tissue stain). Adjacent proximal and distal section segments to the stent were embedded in paraffin, sectioned at four to five microns, and stained with hematoxylin and eosin and Movat's Pentachrome. All sections were examined by light microscopy for the presence of inflammation, thrombus and neointimal formation and vessel wall injury.

FIGS. 8A-8F are views of carotid artery segments of Animal 3. FIGS. 9A-9F are views of carotid artery segments of Animal 6.

Histologic sections were analyzed with an NIST traceable calibrated microscope system (IP Lab software, Rockville, Md.). The cross-sectional areas (external elastic lamina [EEL], internal elastic lamina [IEL], and lumen) of a proximal, mid and distal stented section per segment were measured. Neointimal thickness was measured as the distance from the inner (abluminal) surface of each scaffold strut to the luminal border. Area measurements were used to calculate vessel layer areas with the following formulas:

Medial Area=EEL Area−IEL Area

Neointimal Area=IEL Area−Lumen Area

% Stenosis=[1−(Lumen Area/IEL Area)]*100

Variables were first checked for normal distribution using Shapiro Wilk test then separated into variables with normal and non-parametric distribution. Mean values with standard deviation were derived from normally distributed parameters while non-parametric data were described as median with 25 percent and 75 percent quartiles. In the event of normal distribution, variables were compared using Student's t test or ANOVA with appropriate post hoc corrections for multiple comparisons, when applicable. Wilcoxon rank sum test was used when non-parametric data were compared. A value of p≤0.05 was considered statistically significant.

A morphometric comparison of the cross-sectional vessel areas and neointimal thickness of animals 1-4 and 5-6 is shown in Tables IV and V, below. The comparison includes vessel means±standard deviation of all sections of the vessels (proximal, mid, and distal).

TABLE IV

A morphometric comparison of the cross-sectional vessel areas and neointimal thickness of Animals 1-4 and 5-6. A value of p ≤ 0.05 was considered to be statistically significant.

| Animals | LCCA sections | Lumen Area (mm$^2$) | Medial Area (mm$^2$) |
|---|---|---|---|
| 1-4 | n = 12 | 3.61 ± 0.95 | 0.09 ± 0.09 |
| 5-6 | n = 6 | 2.91 ± 0.58 | 0.05 ± 0.04 |
| p-value | — | 0.0602 | 0.1710 |

TABLE V

A morphometric comparison of the cross-sectional vessel areas and neointimal thickness of Animals 1-4 and 5-6. A value of p ≤ 0.05 was considered to be statistically significant.

| Animals | Neointimal Area (mm$^2$) | Stenosis (%) | Neointimal Thickness (mm) |
|---|---|---|---|
| 1-4 | 2.36 ± 0.54 | 40.25 ± 11.52 | 0.22 ± 0.13 |
| 5-6 | 2.82 ± 0.3 | 49.50 ± 6.66 | 0.36 ± 0.06 |
| p-value | 0.0360 | 0.0450 | 0.0116 |

As indicated in Table V. above, the neointimal area, the stenosis and the neointimal thickness each had a p-value of less than 0.05, thereby indicating that delivering paclitaxel via a drug-coated balloon catheter after laser revascularization of a chronic total occlusion, in comparison to performing balloon angioplasty followed by delivering paclitaxel via a drug-coated balloon catheter, provides an appreciable therapy in maintaining long-term patency for the treatment of peripheral artery disease.

Lesions treated with balloon angioplasty and drug-coated balloon systems tended to show an absence of endothelium within the stent along with plaque debris consisting mainly of macrophage-derived foam cells, free cholesterol, and platelets/fibrin. Chronic inflammatory cell infiltration was also noted within neointimal tissue. The inhibition of the healing response, evidenced by poor endothelialization, along with the presence of fibrin and inflammatory cells suggests a paclitaxel drug effect within this group.

Lesions treated with laser ablation and drug-coated balloon systems also tended to show poor endothelialization with adherent inflammatory cells over underlying fibrotic tissue, which was often acellular. The lumens showed evidence of surface fibrin and/or aggregated fibrin and inflammation with focal areas of neointimal thinning. Fibrin and inflammatory cell staining was implied as being more prominent than in the balloon angioplasty and drug-coated balloon group, which may indicate a stronger paclitaxel drug effect. The higher percentage of patent lumens found in the laser atherectomy and drug-coated balloon group suggests that laser ablation allows for a greater paclitaxel response, the removal of stenotic material prevents reocclusion of the vessel, or a combination thereof.

Stated another way, the results suggest that using a laser system not only removes stenosis, but it also surprisingly and unexpectedly sensitizes the vessel wall to enhance the ability of the drug delivered by a balloon system to reduce the amount of restenosis in comparison to methods that employ balloon angioplasty and drug-coated balloon systems.

Animal Study II.

A second animal study involved six pigs, which were utilized to evaluate the difference in vascular drug uptake between arteries treated with laser ablation prior to drug-coated balloon treatment and arteries treated with balloon angioplasty and drug-coated balloon without laser ablation treatment. On Day 0, each animal (pig) underwent a denudation and vessel over-stretch procedure in the right and left external femoral arteries in an effort to trigger a stenosis response for lesion creation.

Approximately 21 days later the animals underwent another vessel denudation procedure as well as thrombin injection into the vessel to create the total occlusion. Two days following the second denudation procedures, ultrasound was performed to ensure occlusions were intact. However, none of the thrombin induced occlusions were observed to be in place at follow-up. Thrombin was re-dosed four days later and the vessels ligated to enhance stability of the thrombin induced occlusions. The ligatures were removed immediately prior to the treatment procedures. At Day 35 post the initial treatment, the animals underwent the treatment procedures with laser ablation and drug-coated balloon or balloon angioplasty and drug-coated balloon. On Day 49 the animals were humanely euthanized and sent to necropsy. In necropsy, the animals were grossly examined for abnormalities and the treated vessels were harvested for histological analysis.

The study pathologist was blinded during the evaluation. Upon completion of scoring and evaluation, the pathologist was unblinded by the study director for completion of the report. Semi-quantitative morphological observations were recorded to assess the biological response of vascular tissue to treatment. Differences in scoring parameters between the control and test were considered meaningful based on frequency distribution of the grades within each scoring parameter.

One animal (Animal #1) died prematurely within one day after the treatment procedure and one animal (Animal #2) was terminated early (five days after the treatment procedure) due to health issues.

The following abnormalities were noted at necropsy and histopathologically: In Animal #1, a large hematoma was observed surrounding both treated arteries and the left external femoral (LEF) and right external femoral (REF) arteries had a tear in the vessel wall. These findings were histologically correlated with ruptured internal elastic lamina (IEL), media and external elastic lamina (EEL) structures in these arteries. In Animal #2, there was a mass above the LEF treatment site. The mass was filled with fresh and clotted blood. The REF and LEF arteries had a tear in the vessel wall. These findings were histologically correlated with ruptured IEL, media and EEL structures in these arteries. All of these gross and histopathological abnormalities were considered to be related to the treatment procedure and were present in both treatment groups.

Scheduled Animals

The following findings were noted at necropsy and histopathologically: there was firm white tissue (scar) surrounding the treated vessels/access sites noted at necropsy in all animals. This finding was histologically correlated with the presence of adventitial fibrosis and adventitial inflammation and it was considered to be an expected finding related to the surgical procedure. Sections of the REF artery from Animal #3 and the LEF artery from Animal #4 had occlusive thrombus in the lumen. Thrombus generation likely occurred in the vessels after the treatment procedure due to severe vessel wall injury. These samples were not included in the final analysis.

Endothelial Cell Coverage

Endothelial cell coverage was greater in the control and untreated vessel when compared to the test group. Since paclitaxel can inhibit re-endothelialization, the test group likely had greater paclitaxel uptake or exposure to the lumen surface than the control group.

Luminal Thrombus

There was thrombus present in nine of ten ($9/10$) test group sections examined and in two of ten ($2/10$) control sections. Thrombus ranged from minimal to marked. The thrombi in the test group tended to be larger when compared to the control group.

Neointimal Hyperplasia and Maturity

In the test group, some sections had low-maturity neointima. In contrast, in the control group, the neointima was more mature. These differences may be due to greater paclitaxel uptake or greater exposure of the lumen surface to paclitaxel within the test group.

Inflammation

The amount of inflammation in the test group was greater when compared to the control group or untreated vessel. This finding may be due to greater paclitaxel uptake or exposure to paclitaxel in the test group.

Fibrin

The amount of fibrin in the test group was greater when compared to the control group or untreated vessel. This finding was likely due to a greater paclitaxel uptake or exposure of the lumen surface to paclitaxel in the test group.

Medial Smooth Muscle Cell (SMC) loss and Medial Fibrosis (Proteoglycans and Collagen)

Subjectively, medial smooth muscle cell (SMC) loss and the presence of proteoglycans and collagen in the media were greater in the test group when compared to the control group. These differences were likely due to greater paclitaxel uptake or exposure of the lumen surface to paclitaxel in the test group.

Adventitial Fibrosis

Adventitial fibrosis was greater in the test group when compared to the control group. These differences may be due to greater paclitaxel uptake or exposure of the lumen surface to paclitaxel in the test group.

Mineralization

Mineralization was more frequent in the test group when compared to the control group. These differences may be due to greater paclitaxel uptake or exposure of the lumen surface to paclitaxel in the test group.

Results Summary

Lower re-endothelialization, lower neointimal maturity, greater SMC loss, increased collagen/proteoglycans in the media, increased inflammation and increased adventitial fibrosis were all noted in the treatment group as compared to the control group. All of these characteristics have been reported following vascular exposure to paclitaxel ("drug effects"). However, since both groups received the same paclitaxel treatment and since these drug effects were more evident in the treatment group, it is likely that laser atherectomy prior to drug-coated balloon use enhances the paclitaxel related drug effects. This may occur as a result of the removal of atherosclerotic tissue that can act as a barrier to paclitaxel uptake, by the creation of (micro) channels in the atherosclerotic tissue that can facilitate paclitaxel uptake or a combination thereof. Regardless, adjunctive therapy of paclitaxel delivery with a balloon catheter post laser revascularization of a chronic total occlusion (CTO) does appear to show an appreciable treatment effect beyond that of balloon angioplasty and drug-coated balloon, which may provide a translational perspective of this therapy in maintaining long-term patency for the treatment of peripheral artery disease.

Grading

A histopathological grading scale that was used to evaluate each animal is as follows. The results obtained by applying the histopathological grading scale are shown below in Tables VI A and B.

Luminal Thrombus

Luminal thrombus was defined as any thrombus not covered with endothelial cells and consisting of some combination of leukocytes, erythrocytes, platelets and fibrin.
  Grade 0: No luminal thrombus
  Grade 1 (Minimal): Occupies ~<5 percent of the lumen area
  Grade 2 (Mild): Occupies ~5-35 percent of the lumen area
  Grade 3 (Moderate): Occupies ~35-70 percent of the lumen area
  Grade 4 (Severe): Occupies ~>70 percent of the lumen area
Endothelial Cell Coverage
  Grade 0 (Absent): ~<5 percent of the luminal surface covered
  Grade 1 (Minimal): ~5-25 percent of the luminal surface covered
  Grade 2 (Mild): ~25-50 percent of the luminal surface covered
  Grade 3 (Moderate): ~50-90 percent of the luminal surface covered
  Grade 4 (Complete): ~>90 percent of the luminal surface covered
Inflammation
  Grade 0: No inflammatory response
  Grade 1: Minimal response
  Grade 2: Mild response
  Grade 3: Moderate response
  Grade 4: Severe response
Fibrin
  Grade 0: Not present
  Grade 1: Minimal
  Grade 2: Mild
  Grade 3: Moderate
  Grade 4: Severe
SMC Loss
  Grade 0: No medial SMC loss
  Grade 1: Minimal ~<5 percent medial SMC loss
  Grade 2: Mild ~5-25 percent medial SMC loss
  Grade 3: Moderate ~25-50 percent medial SMC loss
  Grade 4: Severe ~>50 percent medial SMC loss
Medial Fibrosis (Proteoglycans and Collagen)
  Grade 0: No changes
  Grade 1: Minimal ~<5 percent of the area with changes
  Grade 2: Mild ~5-25 percent of the area with changes
  Grade 3: Moderate ~25-50 percent of the area with changes
  Grade 4: Severe ~>50 percent of the area with changes
Disruption of the Internal Elastic Lamina (IEL)
  Grade 0: No disruption
  Grade 1: Minimal ~<5 percent disruption
  Grade 2: Mild ~5-25 percent disruption
  Grade 3: Moderate ~25-50 percent disruption
  Grade 4: Severe ~>50 percent disruption
Adventitial Fibrosis
  Grade 0: No changes
  Grade 1: Minimal ~<5 percent of the area with changes
  Grade 2: Mild ~5-25 percent of the area with changes
  Grade 3: Moderate ~25-50 percent of the area with changes
  Grade 4: Severe ~>50 percent of the area with changes
Neointimal Hyperplasia and Maturity
  Grade 0: Not present
  Grade 1: Minimal
  Grade 2: Mild
  Grade 3: Moderate
  Grade 4: Severe
Mineralization
  Grade 0: Not present
  Grade 1: Minimal
  Grade 2: Mild
  Grade 3: Moderate
  Grade 4: Severe

TABLE VI A

Histopathology scoring for Animals 1-6.
A value of $p \leq 0.05$ was considered statistically significant.

| Group | Thrombus | Endothelialization | Neointimal Hyperplasia | Neointimal Maturity | Neointimal Inflammation | Fibrin |
| --- | --- | --- | --- | --- | --- | --- |
| Laser and D-C Ballon- Mean | 2.3 | 2 | 1 | 1.5 | 0.6 | 2.3 |
| Balloon Angioplasty and D-C Ballon- Mean | 0.2 | 2.8 | 1.2 | 2.9 | 0.1 | 0.7 |
| T-test $p \leq 0.05*$ | 0.001* | 0.044* | 0.250 | 0.007* | 0.061 | 0.006* |

As indicated in Table VI A. above, the thrombus, the endothelialization, the neointimal maturity and the fibrin each had a p-value of less than 0.05, thereby indicating that delivering paclitaxel via a drug-coated balloon catheter after laser revascularization of a chronic total occlusion, in comparison to performing balloon angioplasty followed by delivering paclitaxel via a drug-coated balloon catheter, provides an appreciable therapy in maintaining long-term patency for the treatment of peripheral artery disease.

TABLE VI B

Histopathology scoring for Animals 1-6.
A value of p ≤ 0.05 was considered statistically significant.

| Group | IEL disruption | SMC loss | Medial Inflammation | Adventitial Inflammation | Advential Fibrosis | Mineralization |
|---|---|---|---|---|---|---|
| Laser and D-C Ballon-Mean | 2.3 | 2 | 1 | 1.5 | 0.6 | 2.3 |
| Balloon Angioplasty and D-C Ballon-Mean | 0.2 | 2.8 | 1.2 | 2.9 | 0.1 | 0.7 |
| T-test p ≤ 0.05* | 0.001* | 0.044* | 0.250 | 0.007* | 0.061 | 0.006* |

As indicated in Table VI B. above, the adventitial inflammation and the adventitial fibrosis each had a p-value of less than 0.05, thereby indicating that delivering paclitaxel via a drug-coated balloon catheter after laser revascularization of a chronic total occlusion, in comparison to performing balloon angioplasty followed by delivering paclitaxel via a drug-coated balloon catheter, provides an appreciable therapy in maintaining long-term patency for the treatment of peripheral artery disease.

A number of variations and modifications of the disclosure can be used. As a specific example, the methods described above employ separate laser catheters and balloon systems. However, methods according to embodiments of the present disclosure could be performed using a laser catheter and balloon system that are part of a common or "all-in-one" device. As another example, it would be possible to provide for some features of the disclosure without providing others.

The present disclosure, in various aspects, embodiments, and configurations, includes components, methods, processes, systems and/or apparatus substantially as depicted and described herein, including various aspects, embodiments, configurations, subcombinations, and subsets thereof. Those of skill in the art will understand how to make and use the various aspects, aspects, embodiments, and configurations, after understanding the present disclosure. The present disclosure, in various aspects, embodiments, and configurations, includes providing devices and processes in the absence of items not depicted and/or described herein or in various aspects, embodiments, and configurations hereof, including in the absence of such items as may have been used in previous devices or processes, for example, for improving performance, achieving ease and/or reducing cost of implementation.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more, aspects, embodiments and configurations for the purpose of streamlining the disclosure. The features of the aspects, embodiments, and configurations of the disclosure may be combined in alternate aspects, embodiments, and configurations other than those discussed above. This method of disclosure is not to be interpreted as reflecting an intention that the claimed disclosure requires more features than are expressly recited in each claim. Rather, as the following claims reflect, inventive aspects lie in less than all features of a single foregoing disclosed aspects, embodiments, and configurations. Thus, the following claims are hereby incorporated into this Detailed Description, with each claim standing on its own as a separate preferred embodiment of the disclosure.

Moreover, though the description of the disclosure has included description of one or more aspects, embodiments, or configurations and certain variations and modifications, other variations, combinations, and modifications are within the scope of the disclosure, for example, as may be within the skill and knowledge of those in the art, after understanding the present disclosure. It is intended to obtain rights which include alternative aspects, embodiments, and configurations to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A method for treating a target vascular portion of a subject including a stenosis, the method comprising:
   providing a laser ablation system including a laser catheter, the laser catheter including a distal end having a plurality of laser emitters;
   positioning the distal end of the laser catheter within the subject proximate the target vascular portion;
   delivering laser energy to the laser catheter and emitting the laser energy from the plurality of laser emitters to ablate the stenosis, including:
      emitting the laser energy at a first intensity;
      emitting the laser energy at a second intensity, the second intensity being different than the first intensity;
   withdrawing the laser catheter from the subject;
   providing a balloon system including a drug-coated balloon, the drug-coated balloon carrying at least one therapeutic agent, the at least one therapeutic agent being a restenosis inhibitor;
   positioning the drug-coated balloon within the subject proximate the target vascular portion;
   expanding the drug-coated balloon to engage the target vascular portion;
   delivering the at least one therapeutic agent from the drug-coated balloon to the target vascular portion; and
   withdrawing the drug-coated balloon from the subject.

2. The method of claim 1, wherein the restenosis inhibitor includes paclitaxel.

3. The method of claim 1, wherein the laser ablation system includes a laser generator, and further comprising delivering the laser energy from the laser generator to the laser catheter.

4. The method of claim 1, wherein the target vascular portion of the subject includes a stent coupled to the stenosis, and wherein emitting the laser energy from the plurality of laser emitters to ablate the stenosis includes emitting the laser energy from the plurality of laser emitters to ablate the stenosis within the stent.

5. The method of claim 1, wherein the second intensity is greater than the first intensity.

6. The method of claim 1, wherein emitting the laser energy from the plurality of laser emitters to ablate the stenosis includes:
   emitting the laser energy at a first repetition rate; and
   emitting the laser energy at a second repetition rate, the second repetition rate being different than the first repetition rate.

7. The method of claim 6, wherein the second repetition rate is greater than the first repetition rate.

8. A method for treating a target vascular portion of a subject including a stenosis, the method comprising:
   providing a laser ablation system including a first laser catheter including a distal end having a first plurality of laser emitters, the first laser catheter having a first external diameter, the laser ablation system further including a second laser catheter including a distal end having a second plurality of laser emitters, the second laser catheter having a second external diameter, the second external diameter being different than the first external diameter;
   positioning the distal end of the first laser catheter within the subject proximate the target vascular portion;
   delivering laser energy to the first laser catheter and emitting the laser energy from the first plurality of laser emitters to ablate the stenosis;
   withdrawing the first laser catheter from the subject;
   positioning the distal end of the second laser catheter within the subject proximate the target vascular portion;
   delivering laser energy to the second laser catheter and emitting the laser energy from the second plurality of laser emitters to ablate the stenosis;
   withdrawing the second laser catheter from the subject;
   providing a balloon system including a drug-coated balloon, the drug-coated balloon carrying at least one therapeutic agent, the at least one therapeutic agent being a restenosis inhibitor;
   positioning the drug-coated balloon within the subject proximate the target vascular portion;
   expanding the drug-coated balloon to engage the target vascular portion;
   delivering the at least one therapeutic agent from the drug-coated balloon to the target vascular portion; and
   withdrawing the drug-coated balloon from the subject.

9. The method of claim 8, wherein the second external diameter is greater than the first external diameter.

10. A method for treating a target vascular portion of a subject including a stenosis, the method comprising:
   providing a laser ablation system including a laser catheter, the laser catheter including a distal end having a plurality of laser emitters;
   positioning the distal end of the laser catheter within the subject proximate the target vascular portion;
   delivering laser energy to the laser catheter and emitting the laser energy from the plurality of laser emitters to ablate the stenosis, including:
      emitting the laser energy at a first repetition rate;
      emitting the laser energy at a second repetition rate, the second repetition rate being different than the first repetition rate;
   withdrawing the laser catheter from the subject;
   providing a balloon system including a drug-coated balloon, the drug-coated balloon carrying at least one therapeutic agent, the at least one therapeutic agent being a restenosis inhibitor;
   positioning the drug-coated balloon within the subject proximate the target vascular portion;
   expanding the drug-coated balloon to engage the target vascular portion;
   delivering the at least one therapeutic agent from the drug-coated balloon to the target vascular portion; and
   withdrawing the drug-coated balloon from the subject.

11. The method of claim 10, wherein the second repetition rate is greater than the first repetition rate.

12. The method of claim 10, wherein the restenosis inhibitor includes paclitaxel.

13. The method of claim 10, wherein the laser ablation system includes a laser generator, and further comprising delivering the laser energy from the laser generator to the laser catheter.

14. The method of claim 10, wherein the target vascular portion of the subject includes a stent coupled to the stenosis, and wherein emitting the laser energy from the plurality of laser emitters to ablate the stenosis includes emitting the laser energy from the plurality of laser emitters to ablate the stenosis within the stent.

* * * * *